(12) United States Patent
Blomquist et al.

(10) Patent No.: US 11,291,763 B2
(45) Date of Patent: Apr. 5, 2022

(54) BASAL RATE TESTING USING FREQUENT BLOOD GLUCOSE INPUT

(71) Applicant: Tandem Diabetes Care, Inc., San Diego, CA (US)

(72) Inventors: Michael L. Blomquist, Blaine, MN (US); Thomas Alan Savard, Arden Hills, MN (US)

(73) Assignee: Tandem Diabetes Care, Inc., San Diego, CA (US)

( * ) Notice: Subject to any disclaimer, the term of this patent is extended or adjusted under 35 U.S.C. 154(b) by 0 days.

(21) Appl. No.: 15/266,468

(22) Filed: Sep. 15, 2016

(65) Prior Publication Data

US 2017/0000943 A1    Jan. 5, 2017

Related U.S. Application Data

(63) Continuation of application No. 11/685,617, filed on Mar. 13, 2007, now abandoned.

(51) Int. Cl.
*A61M 5/142*       (2006.01)
*A61B 5/145*       (2006.01)
(Continued)

(52) U.S. Cl.
CPC ..... *A61M 5/14244* (2013.01); *A61B 5/14532* (2013.01); *A61B 5/4839* (2013.01);
(Continued)

(58) Field of Classification Search
CPC ........ G16H 20/17; G16H 40/63; G16H 10/60; G16H 20/10; G16H 50/30; A61B 5/14532;
(Continued)

(56) References Cited

U.S. PATENT DOCUMENTS 2,462,596 A    2/1949 Bent
2,629,376 A    2/1953 Pierre et al.
(Continued)

FOREIGN PATENT DOCUMENTS

DE    399065      7/1924
DE    4407005     3/1995
(Continued)

OTHER PUBLICATIONS

IPRP and Written Opinion for International Application No. PCT/US2010/056226 dated Jun. 14, 2012.
(Continued)

*Primary Examiner* — Christian Jang
*Assistant Examiner* — Karen E Toth
(74) *Attorney, Agent, or Firm* — Patterson Thuente Pedersen, P.A.

(57) ABSTRACT

An apparatus comprising a user interface configured to generate an electrical signal to start a basal insulin rate test when prompted by a user, an input configured to receive sampled blood glucose data of a patient that is obtained during a specified time duration, including a time duration during delivery of insulin according to a specified basal insulin rate pattern, and a controller communicatively coupled to the input and the user interface. The controller includes an insulin calculation module configured for determining at least one of an amount of basal insulin over-delivered and an amount of basal insulin under-delivered during the basal insulin rate test in trying to meet a target blood glucose baseline. Other devices and methods are disclosed.

20 Claims, 7 Drawing Sheets

(51) Int. Cl.
*A61B 5/00* (2006.01)
*A61M 5/172* (2006.01)
*G16H 40/63* (2018.01)
*G16H 20/10* (2018.01)

(52) U.S. Cl.
CPC .......... *A61M 5/1723* (2013.01); *G16H 20/10* (2018.01); *G16H 40/63* (2018.01); *A61B 5/14503* (2013.01); *A61M 2005/14208* (2013.01); *A61M 2005/14292* (2013.01); *A61M 2205/502* (2013.01); *A61M 2230/005* (2013.01); *A61M 2230/201* (2013.01)

(58) Field of Classification Search
CPC . A61B 5/4839; A61B 5/14865; A61B 5/7275; A61M 5/1723; A61M 2230/201; A61M 2005/14208
See application file for complete search history.

(56) References Cited

U.S. PATENT DOCUMENTS

| | | |
|---|---|---|
| 2,691,542 A | 10/1954 | Chenoweth |
| 3,059,639 A | 10/1962 | Blackman et al. |
| 4,392,849 A | 7/1983 | Petre et al. |
| 4,393,365 A | 7/1983 | Kondo |
| 4,403,984 A | 9/1983 | Ash et al. |
| 4,475,901 A | 10/1984 | Kraegen et al. |
| 5,000,664 A | 3/1991 | Lawless et al. |
| 5,050,612 A | 9/1991 | Matsumura |
| 5,122,362 A | 6/1992 | Phillips et al. |
| 5,153,827 A | 10/1992 | Coutre et al. |
| 5,181,910 A | 1/1993 | Scanlon |
| 5,207,666 A | 5/1993 | Idriss et al. |
| 5,219,330 A | 6/1993 | Bollish |
| 5,311,175 A | 5/1994 | Waldman |
| 5,338,157 A | 8/1994 | Blomquist |
| 5,362,562 A | 11/1994 | Evans et al. |
| 5,364,346 A | 11/1994 | Schrezenmeir |
| 5,376,070 A | 12/1994 | Purvis et al. |
| 5,389,078 A | 2/1995 | Zalesky et al. |
| 5,395,326 A | 3/1995 | Haber et al. |
| 5,482,446 A | 1/1996 | Williamson et al. |
| 5,485,408 A | 1/1996 | Blomquist |
| 5,551,850 A | 9/1996 | Williamson et al. |
| 5,558,638 A | 9/1996 | Evers et al. |
| 5,569,186 A | 10/1996 | Lord et al. |
| 5,658,250 A | 8/1997 | Blomquist |
| 5,658,252 A | 8/1997 | Johnson |
| 5,665,065 A | 9/1997 | Colman et al. |
| 5,669,877 A | 9/1997 | Blomquist et al. |
| 5,674,240 A | 10/1997 | Bonutti et al. |
| 5,681,285 A | 10/1997 | Ford et al. |
| 5,685,844 A | 11/1997 | Marttila |
| 5,695,473 A | 12/1997 | Olsen |
| 5,713,856 A | 2/1998 | Eggers et al. |
| 5,745,378 A | 4/1998 | Barker et al. |
| 5,782,805 A | 7/1998 | Meinzer |
| 5,810,771 A | 9/1998 | Blomquist |
| 5,814,015 A | 9/1998 | Gargano et al. |
| 5,822,715 A | 10/1998 | Worthington et al. |
| 5,876,370 A | 3/1999 | Blomquist |
| 5,879,143 A | 3/1999 | Cote |
| 5,885,211 A | 3/1999 | Eppstein et al. |
| 5,935,099 A | 8/1999 | Peterson et al. |
| 5,935,106 A | 8/1999 | Olsen |
| 5,960,403 A | 9/1999 | Brown |
| 6,023,629 A | 2/2000 | Tamada |
| 6,024,539 A | 2/2000 | Blomquist |
| 6,077,055 A | 6/2000 | Vilks |
| 6,122,536 A | 9/2000 | Sun et al. |
| 6,142,939 A | 11/2000 | Eppstein et al. |
| 6,175,752 B1 | 1/2001 | Say et al. |
| 6,233,471 B1 | 5/2001 | Berner et al. |
| 6,241,704 B1 | 6/2001 | Peterson et al. |
| 6,248,057 B1 | 6/2001 | Mavity et al. |
| 6,248,067 B1 | 6/2001 | Mavity et al. |
| 6,249,717 B1 | 6/2001 | Nicholson et al. |
| 6,255,781 B1 | 7/2001 | Tsumura |
| 6,272,364 B1 | 8/2001 | Kurnik |
| 6,298,254 B2 | 10/2001 | Tamada |
| 6,306,420 B1 | 10/2001 | Cheikh |
| 6,368,272 B1 | 4/2002 | Porumbescu |
| 6,379,301 B1 | 4/2002 | Worthington et al. |
| 6,422,057 B1 | 7/2002 | Anderson |
| 6,475,180 B2 | 11/2002 | Peterson et al. |
| 6,505,059 B1 | 1/2003 | Kollias et al. |
| 6,517,482 B1 | 2/2003 | Elden et al. |
| 6,535,714 B2 | 3/2003 | Melker et al. |
| 6,539,250 B1 | 3/2003 | Bettinger |
| 6,544,212 B2 | 4/2003 | Galley et al. |
| 6,544,229 B1 | 4/2003 | Danby et al. |
| 6,546,269 B1 | 4/2003 | Kurnik |
| 6,551,276 B1 | 4/2003 | Mann et al. |
| 6,553,244 B2 | 4/2003 | Lesho et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,577,899 B2 | 6/2003 | Lebel et al. |
| 6,582,366 B1 | 6/2003 | Porumbescu |
| 6,595,919 B2 | 7/2003 | Berner et al. |
| 6,623,698 B2 | 9/2003 | Kuo |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,114 B1 | 12/2003 | Poulsen et al. |
| 6,659,978 B1 | 12/2003 | Kasuga et al. |
| 6,668,196 B1 | 12/2003 | Villegas et al. |
| 6,687,522 B2 | 2/2004 | Tamada |
| 6,692,456 B1 | 2/2004 | Eppstein et al. |
| 6,694,191 B2 | 2/2004 | Starkweather et al. |
| 6,740,072 B2 | 5/2004 | Starkweather et al. |
| 6,740,075 B2 | 5/2004 | Lebel et al. |
| 6,744,350 B2 | 6/2004 | Blomquist |
| 6,771,250 B1 | 8/2004 | Oh |
| 6,773,412 B2 | 8/2004 | O'Mahony |
| 6,790,198 B1 | 9/2004 | White et al. |
| 6,809,563 B2 | 10/2004 | Schaal |
| 6,809,653 B1 | 10/2004 | Mann et al. |
| 6,810,290 B2 | 10/2004 | Lebel et al. |
| 6,827,702 B2 | 12/2004 | Lebel et al. |
| 6,835,175 B1 | 12/2004 | Porumbescu |
| 6,852,104 B2 | 2/2005 | Blomquist |
| 6,862,466 B2 | 3/2005 | Ackerman |
| 6,872,200 B2 | 3/2005 | Mann et al. |
| 6,873,268 B2 | 3/2005 | Lebel et al. |
| 6,880,564 B2 | 4/2005 | Erickson |
| 6,882,940 B2 | 4/2005 | Potts et al. |
| 6,902,905 B2 | 6/2005 | Burson et al. |
| 6,918,542 B2 | 7/2005 | Silverbrook et al. |
| 6,934,220 B1 | 8/2005 | Cruitt et al. |
| 6,936,029 B2 | 8/2005 | Mann et al. |
| 6,957,655 B2 | 10/2005 | Erickson et al. |
| 6,958,705 B2 | 10/2005 | Lebel et al. |
| 6,966,325 B2 | 11/2005 | Erickson |
| 6,970,742 B2 | 11/2005 | Mann et al. |
| 6,974,437 B2 | 12/2005 | Lebel et al. |
| 6,979,326 B2 | 12/2005 | Mann et al. |
| 6,997,920 B2 | 2/2006 | Mann et al. |
| 6,998,387 B1 | 2/2006 | Goke et al. |
| 6,999,854 B2 | 2/2006 | Roth |
| 7,004,928 B2 | 2/2006 | Aceti et al. |
| 7,022,072 B2 | 4/2006 | Fox et al. |
| 7,025,743 B2 | 4/2006 | Mann et al. |
| 7,033,338 B2 | 4/2006 | Vilks et al. |
| 7,041,082 B2 | 5/2006 | Blomquist et al. |
| 7,073,713 B2 | 7/2006 | Silverbrook et al. |
| 7,083,108 B2 | 8/2006 | Silverbrook et al. |
| 7,092,011 B2 | 8/2006 | Silverbrook et al. |

(56) References Cited

U.S. PATENT DOCUMENTS

| | | |
|---|---|---|
| 7,097,108 B2 | 8/2006 | Silverbrook et al. |
| 7,098,803 B2 | 8/2006 | Mann et al. |
| 7,109,878 B2 | 9/2006 | Mann et al. |
| 7,150,741 B2 | 12/2006 | Erickson et al. |
| 7,156,808 B2 | 1/2007 | Quy |
| 7,179,226 B2 | 2/2007 | Crothall et al. |
| 7,181,505 B2 | 2/2007 | Haller et al. |
| 7,183,068 B2 | 2/2007 | Burson et al. |
| 7,187,404 B2 | 3/2007 | Silverbrook et al. |
| 7,201,319 B2 | 4/2007 | Silverbrook et al. |
| 7,204,823 B2 | 4/2007 | Estes et al. |
| 7,231,263 B2 | 6/2007 | Choi |
| 7,234,645 B2 | 6/2007 | Silverbrook et al. |
| 7,247,702 B2 | 7/2007 | Gardner et al. |
| 7,254,782 B1 | 8/2007 | Sherer |
| 7,267,665 B2 | 9/2007 | Steil et al. |
| 7,278,983 B2 | 10/2007 | Ireland et al. |
| 7,282,029 B1 | 10/2007 | Poulsen et al. |
| 7,289,142 B2 | 10/2007 | Silverbrook |
| 7,291,107 B2 | 11/2007 | Hellwig et al. |
| 7,295,867 B2 | 11/2007 | Berner et al. |
| 7,307,245 B2 | 12/2007 | Faries et al. |
| 7,320,675 B2 | 1/2008 | Pastore et al. |
| 7,324,012 B2 | 1/2008 | Mann et al. |
| 7,341,577 B2 | 3/2008 | Gill |
| 7,347,836 B2 | 3/2008 | Peterson et al. |
| 7,362,971 B2 | 4/2008 | Silverbrook et al. |
| 7,373,083 B2 | 5/2008 | Silverbrook et al. |
| 7,377,706 B2 | 5/2008 | Silverbrook et al. |
| 7,399,277 B2 | 7/2008 | Saidara et al. |
| 7,404,796 B2 | 7/2008 | Ginsberg |
| 7,446,091 B2 | 11/2008 | Van Den Berghe |
| 7,460,152 B2 | 12/2008 | Silverbrook et al. |
| 7,464,010 B2 | 12/2008 | Yang et al. |
| 7,471,994 B2 | 12/2008 | Ford et al. |
| 7,475,825 B2 | 1/2009 | Silverbrook et al. |
| 7,483,050 B2 | 1/2009 | Silverbrook et al. |
| 7,483,743 B2 | 1/2009 | Mann et al. |
| 7,491,187 B2 | 2/2009 | Van Den Berghe et al. |
| 7,497,827 B2 | 3/2009 | Brister et al. |
| 7,515,060 B2 | 4/2009 | Blomquist |
| 7,524,045 B2 | 4/2009 | Silverbrook et al. |
| 7,534,226 B2 | 5/2009 | Mernoe et al. |
| 7,547,281 B2 | 6/2009 | Hayes et al. |
| 7,553,281 B2 | 6/2009 | Hellwig et al. |
| 7,556,613 B2 | 7/2009 | Wittmann et al. |
| 7,559,926 B1 | 7/2009 | Blischak |
| 7,569,030 B2 | 8/2009 | Lebel et al. |
| 7,572,789 B2 | 8/2009 | Cowen et al. |
| 7,588,046 B1 | 9/2009 | Erickson |
| 7,591,801 B2 | 9/2009 | Brauker et al. |
| 7,602,310 B2 | 10/2009 | Mann et al. |
| 7,647,237 B2 | 1/2010 | Malave et al. |
| 7,651,489 B2 | 1/2010 | Estes et al. |
| 7,651,845 B2 | 1/2010 | Doyle et al. |
| 7,654,976 B2 | 2/2010 | Peterson et al. |
| 7,674,485 B2 | 3/2010 | Bhaskaran et al. |
| 7,676,519 B2 | 3/2010 | Mcbride et al. |
| 7,678,071 B2 | 3/2010 | Lebel et al. |
| 7,678,762 B2 | 3/2010 | Green et al. |
| 7,678,763 B2 | 3/2010 | Green et al. |
| 7,687,272 B1 | 3/2010 | Buchwald et al. |
| 7,697,967 B2 | 4/2010 | Stafford |
| 7,704,226 B2 | 4/2010 | Mueller et al. |
| 7,708,717 B2 | 5/2010 | Estes et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,717,903 B2 | 5/2010 | Estes et al. |
| 7,722,536 B2 | 5/2010 | Goodnow |
| 7,734,323 B2 | 6/2010 | Blomquist et al. |
| 7,751,907 B2 | 7/2010 | Blomquist |
| 7,766,829 B2 | 8/2010 | Sloan et al. |
| 7,766,830 B2 | 8/2010 | Fox et al. |
| 7,768,386 B2 | 8/2010 | Hayter et al. |
| 7,768,408 B2 | 8/2010 | Reggiardo et al. |
| 7,774,145 B2 | 8/2010 | Brauker et al. |
| 7,775,975 B2 | 8/2010 | Brister et al. |
| 7,776,030 B2 | 8/2010 | Estes et al. |
| 7,778,680 B2 | 8/2010 | Goode, Jr. et al. |
| 7,785,313 B2 | 8/2010 | Mastrototaro |
| 7,794,426 B2 | 9/2010 | Briones et al. |
| 7,794,427 B2 | 9/2010 | Estes et al. |
| 7,794,428 B2 | 9/2010 | Estes et al. |
| 7,797,028 B2 | 9/2010 | Goode, Jr. et al. |
| 7,801,582 B2 | 9/2010 | Peyser |
| 7,806,853 B2 | 10/2010 | Wittman et al. |
| 7,806,886 B2 | 10/2010 | Kanderian et al. |
| 7,815,602 B2 | 10/2010 | Mann et al. |
| 7,819,843 B2 | 10/2010 | Mann et al. |
| 7,822,455 B2 | 10/2010 | Hoss et al. |
| 7,826,879 B2 | 11/2010 | Hoss et al. |
| 7,828,528 B2 | 11/2010 | Estes et al. |
| 7,831,310 B2 | 11/2010 | Lebel et al. |
| 7,833,196 B2 | 11/2010 | Estes et al. |
| 7,837,647 B2 | 11/2010 | Estes et al. |
| 7,837,651 B2 | 11/2010 | Bishop et al. |
| 7,850,641 B2 | 12/2010 | Lebel et al. |
| 7,860,544 B2 | 12/2010 | Say et al. |
| 7,869,851 B2 | 1/2011 | Hellwig et al. |
| 7,869,853 B1 | 1/2011 | Say et al. |
| 7,875,022 B2 | 1/2011 | Wenger et al. |
| 7,884,729 B2 | 2/2011 | Reggiardo et al. |
| 7,885,699 B2 | 2/2011 | Say et al. |
| 7,887,512 B2 | 2/2011 | Estes et al. |
| 7,890,295 B2 | 2/2011 | Shin et al. |
| 7,892,199 B2 | 2/2011 | Mhatre et al. |
| 7,912,674 B2 | 3/2011 | Killoren et al. |
| 7,914,450 B2 | 3/2011 | Goode, Jr. et al. |
| 7,914,499 B2 | 3/2011 | Gonnelli et al. |
| 7,920,907 B2 | 4/2011 | McGarraugh et al. |
| 7,933,780 B2 | 4/2011 | De La Huerga |
| 7,935,076 B2 | 5/2011 | Estes et al. |
| 7,938,797 B2 | 5/2011 | Estes |
| 7,938,803 B2 | 5/2011 | Mernoe et al. |
| 7,941,200 B2 | 5/2011 | Weinert et al. |
| 7,946,985 B2 | 5/2011 | Mastrototaro et al. |
| 7,951,114 B2 | 5/2011 | Rush et al. |
| 7,959,598 B2 | 6/2011 | Estes |
| 7,963,946 B2 | 6/2011 | Moubayed et al. |
| 7,967,773 B2 | 6/2011 | Amborn et al. |
| 7,972,296 B2 | 7/2011 | Braig et al. |
| 7,976,492 B2 | 7/2011 | Brauker et al. |
| 7,981,034 B2 | 7/2011 | Jennewine et al. |
| 7,981,084 B2 | 7/2011 | Estes et al. |
| 7,981,102 B2 | 7/2011 | Patel et al. |
| 7,983,745 B2 | 7/2011 | Hatlestad et al. |
| 7,983,759 B2 | 7/2011 | Stahmann et al. |
| 7,985,330 B2 | 7/2011 | Wang et al. |
| 7,988,630 B1 | 8/2011 | Osorio et al. |
| 7,988,849 B2 | 8/2011 | Biewer et al. |
| 7,996,158 B2 | 8/2011 | Hayter et al. |
| 8,005,524 B2 | 8/2011 | Brauker et al. |
| 8,012,119 B2 | 9/2011 | Estes et al. |
| 8,016,783 B2 | 9/2011 | Pastore et al. |
| 8,025,634 B1 | 9/2011 | Moubayed et al. |
| 8,029,459 B2 | 10/2011 | Rush et al. |
| 8,029,460 B2 | 10/2011 | Rush et al. |
| 8,062,249 B2 | 11/2011 | Wilinska et al. |
| 8,066,665 B2 | 11/2011 | Rush et al. |
| 8,075,527 B2 | 12/2011 | Rush et al. |
| 8,079,983 B2 | 12/2011 | Rush et al. |
| 8,079,984 B2 | 12/2011 | Rush et al. |
| 8,083,718 B2 | 12/2011 | Rush et al. |
| 8,088,098 B2 | 1/2012 | Yodfat et al. |
| 8,093,212 B2 | 1/2012 | Gardner et al. |
| 8,105,268 B2 | 1/2012 | Lebel et al. |
| 8,105,279 B2 | 1/2012 | Mernoe et al. |
| 8,109,921 B2 | 2/2012 | Estes et al. |
| 8,114,350 B1 | 2/2012 | Silver et al. |
| 8,118,770 B2 | 2/2012 | Galley et al. |
| 8,119,593 B2 | 2/2012 | Richardson et al. |
| 8,127,046 B2 | 2/2012 | Grant et al. |
| 8,129,429 B2 | 3/2012 | Sporn et al. |

(56) References Cited

U.S. PATENT DOCUMENTS

| | | |
|---|---|---|
| 8,133,197 B2 | 3/2012 | Blomquist et al. |
| 8,140,275 B2 | 3/2012 | Campbell et al. |
| 8,140,312 B2 | 3/2012 | Hayter et al. |
| RE43,316 E | 4/2012 | Brown et al. |
| 8,147,446 B2 | 4/2012 | Yodfat et al. |
| 8,152,789 B2 | 4/2012 | Starkweather et al. |
| 8,170,721 B2 | 5/2012 | Nickerson |
| 8,177,716 B2 | 5/2012 | Say et al. |
| 8,182,445 B2 | 5/2012 | Moubayed et al. |
| 8,192,394 B2 | 6/2012 | Estes et al. |
| 8,202,267 B2 | 6/2012 | Field et al. |
| 8,204,729 B2 | 6/2012 | Sher |
| 8,206,296 B2 | 6/2012 | Jennewine |
| 8,206,350 B2 | 6/2012 | Mann et al. |
| 8,208,984 B2 | 6/2012 | Blomquist |
| 8,211,062 B2 | 7/2012 | Estes et al. |
| 8,219,222 B2 | 7/2012 | Blomquist |
| 8,221,345 B2 | 7/2012 | Blomquist |
| 8,221,385 B2 | 7/2012 | Estes |
| 8,226,558 B2 | 7/2012 | Say et al. |
| 8,234,126 B1 | 7/2012 | Estes |
| 8,234,128 B2 | 7/2012 | Martucci et al. |
| 8,237,715 B2 | 8/2012 | Buck et al. |
| 8,246,540 B2 | 8/2012 | Ginsberg |
| 8,250,483 B2 | 8/2012 | Blomquist |
| 8,251,904 B2 | 8/2012 | Zivitz et al. |
| 8,251,906 B2 | 8/2012 | Brauker et al. |
| 8,257,259 B2 | 9/2012 | Brauker et al. |
| 8,257,300 B2 | 9/2012 | Budiman et al. |
| 8,260,630 B2 | 9/2012 | Brown |
| 8,262,617 B2 | 9/2012 | Aeschlimann et al. |
| 8,277,435 B2 | 10/2012 | Estes |
| 8,282,601 B2 | 10/2012 | Mernoe et al. |
| 8,287,454 B2 | 10/2012 | Wolpert et al. |
| 8,287,495 B2 | 10/2012 | Michaud et al. |
| 8,287,514 B2 | 10/2012 | Miller et al. |
| 8,290,562 B2 | 10/2012 | Goode, Jr. et al. |
| 8,298,184 B2 | 10/2012 | Diperna et al. |
| 8,311,749 B2 | 11/2012 | Brauker et al. |
| 8,323,188 B2 | 12/2012 | Tran |
| 8,326,546 B2 | 12/2012 | Stewart et al. |
| 8,328,754 B2 | 12/2012 | Estes et al. |
| 8,343,092 B2 | 1/2013 | Rush et al. |
| 8,344,847 B2 | 1/2013 | Moberg et al. |
| 8,346,399 B2 | 1/2013 | Blomquist |
| 8,348,885 B2 | 1/2013 | Moberg et al. |
| 8,349,319 B2 | 1/2013 | Schuchman et al. |
| 8,357,091 B2 | 1/2013 | Say et al. |
| 8,369,919 B2 | 2/2013 | Kamath |
| 8,372,040 B2 | 2/2013 | Huang et al. |
| 8,376,943 B2 | 2/2013 | Kovach et al. |
| 8,377,031 B2 | 2/2013 | Hayter et al. |
| 8,380,273 B2 | 2/2013 | Say et al. |
| 8,409,131 B2 | 4/2013 | Say et al. |
| 8,414,523 B2 | 4/2013 | Blomquist et al. |
| 8,444,595 B2 | 5/2013 | Brukalo et al. |
| 8,451,230 B2 | 5/2013 | Celentano et al. |
| 8,452,953 B2 | 5/2013 | Buck et al. |
| 8,454,510 B2 | 6/2013 | Yodfat et al. |
| 8,454,575 B2 | 6/2013 | Estes et al. |
| 8,454,576 B2 | 6/2013 | Mastrototaro et al. |
| 8,454,581 B2 | 6/2013 | Estes et al. |
| 8,460,231 B2 | 6/2013 | Brauker et al. |
| 8,467,980 B2 | 6/2013 | Campbell et al. |
| 8,562,558 B2 | 7/2013 | Yodfat et al. |
| 8,449,523 B2 | 8/2013 | Brukalo et al. |
| 8,552,880 B2 | 10/2013 | Kopp et al. |
| 8,573,027 B2 | 11/2013 | Rosinko |
| 8,579,853 B2 | 11/2013 | Reggiardo et al. |
| 8,650,937 B2 | 2/2014 | Brown |
| 8,657,779 B2 | 2/2014 | Blomquist |
| 8,712,748 B2 | 4/2014 | Thukral et al. |
| 8,718,949 B2 | 5/2014 | Blomquist et al. |
| 8,726,266 B2 | 5/2014 | Kiaie |
| 8,775,877 B2 | 7/2014 | McVey et al. |
| 8,798,934 B2 * | 8/2014 | Wei ............ A61B 5/746 |
| | | 702/19 |
| 8,801,657 B2 | 8/2014 | Blomquist et al. |
| 8,852,152 B2 | 10/2014 | Tverskoy |
| 8,882,701 B2 | 11/2014 | DeBelser et al. |
| 8,986,253 B2 | 3/2015 | DiPerna |
| 9,008,803 B2 | 4/2015 | Blomquist |
| 9,037,254 B2 | 5/2015 | John |
| 9,364,679 B2 | 6/2016 | John |
| 9,474,856 B2 | 10/2016 | Blomquist |
| 9,486,171 B2 | 11/2016 | Saint |
| 9,669,160 B2 | 6/2017 | Harris et al. |
| 2001/0001144 A1 | 5/2001 | Kapp |
| 2001/0031944 A1 | 10/2001 | Peterson et al. |
| 2001/0037217 A1 | 11/2001 | Abensour et al. |
| 2001/0041831 A1 | 11/2001 | Starkweather |
| 2002/0002326 A1 | 1/2002 | Causey, III et al. |
| 2002/0065454 A1 | 5/2002 | Lebel et al. |
| 2002/0072932 A1 | 6/2002 | Swamy |
| 2002/0077852 A1 | 6/2002 | Ford et al. |
| 2002/0107476 A1 | 8/2002 | Mann et al. |
| 2002/0143580 A1 | 10/2002 | Bristol et al. |
| 2002/0183693 A1 | 12/2002 | Peterson et al. |
| 2002/0193679 A1 | 12/2002 | Malave et al. |
| 2003/0032867 A1 | 2/2003 | Crothall et al. |
| 2003/0036683 A1 | 2/2003 | Kehr et al. |
| 2003/0161744 A1 | 2/2003 | Vilks et al. |
| 2003/0055323 A1 | 3/2003 | Choi |
| 2003/0060765 A1 | 3/2003 | Campbell et al. |
| 2003/0065308 A1 | 4/2003 | Lebel et al. |
| 2003/0088238 A1 | 5/2003 | Poulsen et al. |
| 2003/0104982 A1 | 6/2003 | Wittman et al. |
| 2003/0114836 A1* | 6/2003 | Estes .......... A61M 5/14244 |
| | | 604/890.1 |
| 2003/0130616 A1 | 7/2003 | Steil et al. |
| 2003/0145854 A1 | 8/2003 | Hickle |
| 2003/0159945 A1 | 8/2003 | Miyazaki |
| 2003/0160683 A1 | 8/2003 | Blomquist |
| 2003/0163088 A1 | 8/2003 | Blomquist |
| 2003/0163090 A1 | 8/2003 | Blomquist et al. |
| 2003/0163223 A1 | 8/2003 | Blomquist |
| 2003/0163789 A1 | 8/2003 | Blomquist |
| 2003/0199854 A1 | 10/2003 | Kovach et al. |
| 2003/0208113 A1 | 11/2003 | Mault et al. |
| 2003/0211617 A1 | 11/2003 | Jones |
| 2003/0212364 A1 | 11/2003 | Mann et al. |
| 2003/0212379 A1 | 11/2003 | Bylund et al. |
| 2003/0236489 A1 | 12/2003 | Jacobson et al. |
| 2004/0015132 A1 | 1/2004 | Brown |
| 2004/0054263 A1 | 3/2004 | Moerman et al. |
| 2004/0073095 A1 | 4/2004 | Causey, III et al. |
| 2004/0115067 A1 | 6/2004 | Rush et al. |
| 2004/0152622 A1 | 8/2004 | Keith |
| 2004/0167464 A1 | 8/2004 | Ireland |
| 2004/0180810 A1 | 9/2004 | Pilarski |
| 2004/0193025 A1 | 9/2004 | Steil et al. |
| 2004/0193090 A1 | 9/2004 | Lebel et al. |
| 2004/0199409 A1* | 10/2004 | Brown ............ G16H 40/40 |
| | | 705/3 |
| 2004/0220517 A1* | 11/2004 | Starkweather ....... A61M 5/172 |
| | | 604/67 |
| 2004/0225252 A1 | 11/2004 | Gillespie, Jr. et al. |
| 2004/0254434 A1 | 12/2004 | Goodnow et al. |
| 2005/0021006 A1 | 1/2005 | Tonnies |
| 2005/0022274 A1 | 1/2005 | Campbell et al. |
| 2005/0027182 A1 | 2/2005 | Siddiqui et al. |
| 2005/0030164 A1 | 2/2005 | Blomquist |
| 2005/0038332 A1 | 2/2005 | Saidara et al. |
| 2005/0050621 A1 | 3/2005 | Thomas |
| 2005/0065464 A1 | 3/2005 | Talbot et al. |
| 2005/0065760 A1 | 3/2005 | Murtfeldt et al. |
| 2005/0081847 A1 | 4/2005 | Lee et al. |
| 2005/0095063 A1 | 5/2005 | Fathallah et al. |
| 2005/0137530 A1 | 6/2005 | Campbell et al. |
| 2005/0143864 A1 | 6/2005 | Blomquist |
| 2005/0159656 A1 | 7/2005 | Hockersmith et al. |
| 2005/0171513 A1 | 8/2005 | Mann et al. |
| 2005/0182358 A1 | 8/2005 | Veit |
| 2005/0192557 A1 | 9/2005 | Brauker et al. |

(56) References Cited

U.S. PATENT DOCUMENTS

| | | |
|---|---|---|
| 2005/0197553 A1 | 9/2005 | Cooper |
| 2005/0197621 A1 | 9/2005 | Poulsen et al. |
| 2005/0203349 A1 | 9/2005 | Nanikashvili |
| 2005/0228234 A1 | 10/2005 | Yang |
| 2005/0272640 A1 | 12/2005 | Doyle, III et al. |
| 2005/0277872 A1 | 12/2005 | Colby et al. |
| 2005/0277912 A1 | 12/2005 | John |
| 2006/0001538 A1 | 1/2006 | Kraft et al. |
| 2006/0001550 A1 | 1/2006 | Mann et al. |
| 2006/0010098 A1 | 1/2006 | Goodnow |
| 2006/0014670 A1 | 1/2006 | Green et al. |
| 2006/0031094 A1 | 2/2006 | Cohen et al. |
| 2006/0047192 A1 | 3/2006 | Hellwig et al. |
| 2006/0047538 A1 | 3/2006 | Condurso et al. |
| 2006/0080059 A1 | 4/2006 | Stupp et al. |
| 2006/0085223 A1 | 4/2006 | Anderson |
| 2006/0093785 A1 | 5/2006 | Hickle |
| 2006/0094985 A1 | 5/2006 | Aceti et al. |
| 2006/0122577 A1 | 6/2006 | Poulsen et al. |
| 2006/0132292 A1 | 6/2006 | Blomquist |
| 2006/0137695 A1 | 6/2006 | Hellwig et al. |
| 2006/0167345 A1 | 7/2006 | Vespasiani |
| 2006/0173406 A1 | 8/2006 | Hayes et al. |
| 2006/0173444 A1 | 8/2006 | Choy et al. |
| 2006/0202859 A1 | 9/2006 | Mastrototaro et al. |
| 2006/0224109 A1* | 10/2006 | Steil ............... A61B 5/14532 604/66 |
| 2006/0253097 A1 | 11/2006 | Braig et al. |
| 2006/0253296 A1 | 11/2006 | Liisberg et al. |
| 2006/0264895 A1 | 11/2006 | Flanders |
| 2006/0271020 A1 | 11/2006 | Huang et al. |
| 2006/0272652 A1 | 12/2006 | Stocker |
| 2006/0276771 A1 | 12/2006 | Galley et al. |
| 2007/0010950 A1 | 1/2007 | Abensour et al. |
| 2007/0016127 A1 | 1/2007 | Staib et al. |
| 2007/0016170 A1 | 1/2007 | Kovelman |
| 2007/0016449 A1 | 1/2007 | Cohen et al. |
| 2007/0021733 A1 | 1/2007 | Hansen et al. |
| 2007/0033074 A1 | 2/2007 | Nitzan et al. |
| 2007/0060796 A1 | 3/2007 | Kim |
| 2007/0060871 A1 | 3/2007 | Istoc |
| 2007/0060874 A1 | 3/2007 | Nesbitt et al. |
| 2007/0066956 A1 | 3/2007 | Finkel |
| 2007/0073236 A1 | 3/2007 | Mernoe et al. |
| 2007/0078314 A1 | 4/2007 | Grounsell et al. |
| 2007/0083152 A1 | 4/2007 | Williams, Jr. |
| 2007/0083335 A1 | 4/2007 | Moerman |
| 2007/0093786 A1 | 4/2007 | Goldsmith et al. |
| 2007/0100222 A1 | 5/2007 | Mastrototaro et al. |
| 2007/0106135 A1* | 5/2007 | Sloan ............... A61B 5/14532 600/322 |
| 2007/0112298 A1 | 5/2007 | Mueller, Jr. et al. |
| 2007/0112299 A1 | 5/2007 | Smit et al. |
| 2007/0118405 A1 | 5/2007 | Campbell et al. |
| 2007/0124002 A1 | 5/2007 | Estes et al. |
| 2007/0149861 A1 | 6/2007 | Crothall et al. |
| 2007/0156033 A1 | 7/2007 | Causey, III et al. |
| 2007/0156092 A1 | 7/2007 | Estes et al. |
| 2007/0156457 A1 | 7/2007 | Brown |
| 2007/0167905 A1 | 7/2007 | Estes et al. |
| 2007/0167912 A1 | 7/2007 | Causey et al. |
| 2007/0173712 A1 | 7/2007 | Shah et al. |
| 2007/0173762 A1 | 7/2007 | Estes et al. |
| 2007/0179355 A1 | 8/2007 | Rosen |
| 2007/0179444 A1 | 8/2007 | Causey et al. |
| 2007/0203454 A1 | 8/2007 | Shermer et al. |
| 2007/0213657 A1* | 9/2007 | Jennewine ............ A61B 5/0031 604/66 |
| 2007/0233051 A1 | 10/2007 | Hohl et al. |
| 2007/0245258 A1 | 10/2007 | Ginggen et al. |
| 2007/0251835 A1 | 11/2007 | Mehta et al. |
| 2007/0253021 A1 | 11/2007 | Mehta et al. |
| 2007/0253380 A1 | 11/2007 | Jollota et al. |
| 2007/0254593 A1 | 11/2007 | Jollota et al. |
| 2007/0255116 A1 | 11/2007 | Mehta et al. |
| 2007/0255125 A1 | 11/2007 | Moberg et al. |
| 2007/0255126 A1 | 11/2007 | Moberg et al. |
| 2007/0255250 A1 | 11/2007 | Moberg et al. |
| 2007/0255348 A1 | 11/2007 | Holtzclaw |
| 2007/0258395 A1 | 11/2007 | Jollota et al. |
| 2007/0287985 A1 | 12/2007 | Estes |
| 2007/0299389 A1 | 12/2007 | Halbert et al. |
| 2008/0004601 A1 | 1/2008 | Jennewine et al. |
| 2008/0030369 A1 | 2/2008 | Mann et al. |
| 2008/0033357 A1 | 2/2008 | Mann et al. |
| 2008/0033360 A1 | 2/2008 | Evans et al. |
| 2008/0033361 A1 | 2/2008 | Evans et al. |
| 2008/0045902 A1 | 2/2008 | Estes et al. |
| 2008/0045903 A1 | 2/2008 | Estes et al. |
| 2008/0045904 A1 | 2/2008 | Estes et al. |
| 2008/0045931 A1 | 2/2008 | Estes et al. |
| 2008/0051709 A1 | 2/2008 | Mounce et al. |
| 2008/0051714 A1 | 2/2008 | Moberg et al. |
| 2008/0051716 A1 | 2/2008 | Stutz |
| 2008/0058773 A1 | 3/2008 | John |
| 2008/0065007 A1 | 3/2008 | Peterson |
| 2008/0065016 A1 | 3/2008 | Peterson et al. |
| 2008/0071209 A1 | 3/2008 | Moubayed |
| 2008/0071210 A1 | 3/2008 | Moubayed |
| 2008/0071217 A1 | 3/2008 | Moubayed |
| 2008/0071251 A1 | 3/2008 | Moubayed |
| 2008/0071580 A1 | 3/2008 | Marcus et al. |
| 2008/0076969 A1 | 3/2008 | Kraft et al. |
| 2008/0097289 A1 | 4/2008 | Steil et al. |
| 2008/0106431 A1* | 5/2008 | Blomquist ......... A61M 5/14566 340/4.13 |
| 2008/0114299 A1 | 5/2008 | Damgaard-Sorensen et al. |
| 2008/0132844 A1 | 6/2008 | Peterson |
| 2008/0139907 A1 | 6/2008 | Rao et al. |
| 2008/0139910 A1 | 6/2008 | Mastrototaro et al. |
| 2008/0147004 A1 | 6/2008 | Mann et al. |
| 2008/0147041 A1 | 6/2008 | Kristensen et al. |
| 2008/0147050 A1 | 6/2008 | Mann et al. |
| 2008/0154513 A1 | 6/2008 | Kovatchev et al. |
| 2008/0156661 A1 | 7/2008 | Cooper et al. |
| 2008/0171697 A1 | 7/2008 | Jacotot et al. |
| 2008/0171967 A1 | 7/2008 | Blomquist et al. |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1 | 7/2008 | Blomquist |
| 2008/0177165 A1 | 7/2008 | Blomquist |
| 2008/0183060 A1 | 7/2008 | Steil et al. |
| 2008/0206799 A1 | 8/2008 | Blomquist |
| 2008/0228055 A1 | 9/2008 | Sher |
| 2008/0228056 A1 | 9/2008 | Blomquist et al. |
| 2008/0249470 A1 | 10/2008 | Malave et al. |
| 2008/0255438 A1 | 10/2008 | Saidara et al. |
| 2008/0255517 A1 | 10/2008 | Nair et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0264024 A1 | 11/2008 | Cosentino et al. |
| 2008/0287922 A1 | 11/2008 | Panduro |
| 2008/0288115 A1 | 11/2008 | Rusnak et al. |
| 2008/0294094 A1 | 11/2008 | Mhatre et al. |
| 2008/0294108 A1 | 11/2008 | Briones et al. |
| 2008/0294109 A1 | 11/2008 | Estes et al. |
| 2008/0294142 A1 | 11/2008 | Patel |
| 2008/0294294 A1 | 11/2008 | Blomquist |
| 2008/0300534 A1 | 12/2008 | Blomquist |
| 2008/0300572 A1 | 12/2008 | Dobbles et al. |
| 2008/0300651 A1 | 12/2008 | Gerber et al. |
| 2008/0306353 A1 | 12/2008 | Douglas et al. |
| 2008/0306434 A1 | 12/2008 | Dobbles et al. |
| 2008/0306444 A1 | 12/2008 | Brister et al. |
| 2008/0312584 A1 | 12/2008 | Montgomery et al. |
| 2008/0312585 A1 | 12/2008 | Brukalo et al. |
| 2009/0005726 A1 | 1/2009 | Jones et al. |
| 2009/0018779 A1 | 1/2009 | Cohen et al. |
| 2009/0030733 A1 | 1/2009 | Cohen et al. |
| 2009/0036753 A1 | 2/2009 | King |

(56) References Cited

U.S. PATENT DOCUMENTS

| | | |
|---|---|---|
| 2009/0067989 A1 | 3/2009 | Estes et al. |
| 2009/0069745 A1 | 3/2009 | Estes et al. |
| 2009/0069749 A1 | 3/2009 | Miller et al. |
| 2009/0069787 A1 | 3/2009 | Estes et al. |
| 2009/0085768 A1 | 4/2009 | Patel et al. |
| 2009/0088731 A1 | 4/2009 | Campbell et al. |
| 2009/0093756 A1 | 4/2009 | Minaie |
| 2009/0105636 A1 | 4/2009 | Hayter |
| 2009/0105646 A1 | 4/2009 | Hendrixson et al. |
| 2009/0112626 A1 | 4/2009 | Talbot et al. |
| 2009/0118592 A1 | 5/2009 | Klitgaard |
| 2009/0131860 A1 | 5/2009 | Nielsen |
| 2009/0131861 A1 | 5/2009 | Braig et al. |
| 2009/0143661 A1 | 6/2009 | Taub et al. |
| 2009/0150186 A1 | 6/2009 | Cohen et al. |
| 2009/0150865 A1 | 6/2009 | Young et al. |
| 2009/0156990 A1 | 6/2009 | Wenger et al. |
| 2009/0157003 A1 | 6/2009 | Jones et al. |
| 2009/0163855 A1 | 6/2009 | Shin et al. |
| 2009/0171269 A1 | 7/2009 | Jennewine et al. |
| 2009/0177142 A1 | 7/2009 | Blomquist et al. |
| 2009/0177147 A1 | 7/2009 | Blomquist et al. |
| 2009/0177154 A1 | 7/2009 | Blomquist |
| 2009/0177180 A1 | 7/2009 | Rubalcaba |
| 2009/0192366 A1 | 7/2009 | Mensinger et al. |
| 2009/0192724 A1 | 7/2009 | Brauker et al. |
| 2009/0192745 A1 | 7/2009 | Kamath et al. |
| 2009/0212966 A1 | 8/2009 | Panduro |
| 2009/0216100 A1 | 8/2009 | Ebner et al. |
| 2009/0240193 A1 | 9/2009 | Mensinger et al. |
| 2009/0247931 A1 | 10/2009 | Damgaard-Sorensen |
| 2009/0247982 A1 | 10/2009 | Krulevitch et al. |
| 2009/0254037 A1 | 10/2009 | Bryant, Jr. et al. |
| 2009/0267775 A1 | 10/2009 | Enegren et al. |
| 2009/0270705 A1 | 10/2009 | Enegren et al. |
| 2009/0270810 A1 | 10/2009 | Debelser et al. |
| 2009/0275886 A1 | 11/2009 | Blomquist et al. |
| 2009/0275887 A1 | 11/2009 | Estes |
| 2009/0281393 A1 | 11/2009 | Smith |
| 2010/0008795 A1 | 1/2010 | DiPerna |
| 2010/0010330 A1 | 1/2010 | Rankers et al. |
| 2010/0030045 A1 | 2/2010 | Gottlieb et al. |
| 2010/0030387 A1 | 2/2010 | Sen |
| 2010/0049164 A1 | 2/2010 | Estes |
| 2010/0056993 A1 | 3/2010 | Chase |
| 2010/0057043 A1 | 3/2010 | Kovatchev et al. |
| 2010/0064257 A1 | 3/2010 | Buck et al. |
| 2010/0069730 A1 | 3/2010 | Bergstrom |
| 2010/0081993 A1 | 4/2010 | O'Connor |
| 2010/0094110 A1 | 4/2010 | Heller |
| 2010/0094251 A1 | 4/2010 | Estes |
| 2010/0095229 A1 | 4/2010 | Dixon et al. |
| 2010/0105999 A1 | 4/2010 | Dixon et al. |
| 2010/0114015 A1 | 5/2010 | Kanderian, Jr. et al. |
| 2010/0121169 A1 | 5/2010 | Petisce et al. |
| 2010/0121170 A1 | 5/2010 | Rule |
| 2010/0125241 A1 | 5/2010 | Prud et al. |
| 2010/0130933 A1 | 5/2010 | Holland et al. |
| 2010/0138197 A1 | 6/2010 | Sher |
| 2010/0145173 A1* | 6/2010 | Alferness .............. G16H 50/50 600/365 |
| 2010/0145276 A1 | 6/2010 | Yodfat et al. |
| 2010/0145303 A1 | 6/2010 | Yodfat et al. |
| 2010/0156633 A1 | 6/2010 | Buck et al. |
| 2010/0160740 A1 | 6/2010 | Cohen et al. |
| 2010/0161236 A1 | 6/2010 | Cohen et al. |
| 2010/0161346 A1 | 6/2010 | Getschmann et al. |
| 2010/0162786 A1 | 7/2010 | Keenan et al. |
| 2010/0174266 A1 | 7/2010 | Estes |
| 2010/0174553 A1 | 7/2010 | Kaufman et al. |
| 2010/0179402 A1 | 7/2010 | Goode et al. |
| 2010/0185142 A1 | 7/2010 | Kamen et al. |
| 2010/0185175 A1 | 7/2010 | Kamen et al. |
| 2010/0192686 A1 | 8/2010 | Kamen et al. |
| 2010/0198034 A1 | 8/2010 | Thomas et al. |
| 2010/0198142 A1 | 8/2010 | Sloan et al. |
| 2010/0202040 A1 | 8/2010 | Morgan |
| 2010/0205001 A1 | 8/2010 | Knudsen et al. |
| 2010/0218132 A1 | 8/2010 | Soni et al. |
| 2010/0222765 A1 | 9/2010 | Blomquist et al. |
| 2010/0228186 A1 | 9/2010 | Estes et al. |
| 2010/0234709 A1 | 9/2010 | Say et al. |
| 2010/0235439 A1 | 9/2010 | Goodnow |
| 2010/0249530 A1 | 9/2010 | Rankers et al. |
| 2010/0249561 A1 | 9/2010 | Patek et al. |
| 2010/0261987 A1 | 10/2010 | Kamath et al. |
| 2010/0262078 A1 | 10/2010 | Blomquist |
| 2010/0262117 A1 | 10/2010 | Magni et al. |
| 2010/0262434 A1 | 10/2010 | Shaya |
| 2010/0274592 A1 | 10/2010 | Nitzan et al. |
| 2010/0274751 A1 | 10/2010 | Blomquist |
| 2010/0277119 A1 | 11/2010 | Montague et al. |
| 2010/0280329 A1 | 11/2010 | Randløv et al. |
| 2010/0286563 A1 | 11/2010 | Bryer et al. |
| 2010/0286601 A1 | 11/2010 | Yodfat et al. |
| 2010/0286653 A1 | 11/2010 | Kubel et al. |
| 2010/0292634 A1 | 11/2010 | Kircher, Jr. et al. |
| 2010/0295686 A1 | 11/2010 | Sloan et al. |
| 2010/0298681 A1 | 11/2010 | Say et al. |
| 2010/0298685 A1 | 11/2010 | Hayter et al. |
| 2010/0305421 A1 | 12/2010 | Ow-Wing |
| 2010/0305545 A1 | 12/2010 | Kanderian, Jr. et al. |
| 2010/0305965 A1 | 12/2010 | Benjamin et al. |
| 2010/0312085 A1 | 12/2010 | Andrews et al. |
| 2010/0324382 A1 | 12/2010 | Cantwell et al. |
| 2010/0324398 A1 | 12/2010 | Tzyy-Ping |
| 2010/0324932 A1 | 12/2010 | Galley et al. |
| 2010/0331651 A1 | 12/2010 | Groll |
| 2011/0004188 A1 | 1/2011 | Shekalim |
| 2011/0006876 A1 | 1/2011 | Moberg et al. |
| 2011/0009725 A1 | 1/2011 | Hill et al. |
| 2011/0009813 A1 | 1/2011 | Rankers |
| 2011/0010105 A1 | 1/2011 | Shah et al. |
| 2011/0015509 A1 | 1/2011 | Peyser |
| 2011/0021898 A1 | 1/2011 | Wei et al. |
| 2011/0022025 A1 | 1/2011 | Savoie et al. |
| 2011/0033833 A1 | 2/2011 | Blomquist et al. |
| 2011/0040247 A1 | 2/2011 | Mandro et al. |
| 2011/0040251 A1 | 2/2011 | Blomquist |
| 2011/0046051 A1 | 2/2011 | Moerman |
| 2011/0046892 A1 | 2/2011 | Moerman |
| 2011/0047499 A1 | 2/2011 | Mandro et al. |
| 2011/0048938 A1 | 3/2011 | Shah et al. |
| 2011/0048941 A1 | 3/2011 | Shah et al. |
| 2011/0050428 A1 | 3/2011 | Istoc |
| 2011/0053121 A1 | 3/2011 | Heaton |
| 2011/0054281 A1 | 3/2011 | Shah et al. |
| 2011/0054390 A1 | 3/2011 | Searle et al. |
| 2011/0054391 A1 | 3/2011 | Ward et al. |
| 2011/0056264 A1 | 3/2011 | Kaplan |
| 2011/0058485 A1 | 3/2011 | Sloan |
| 2011/0060281 A1 | 3/2011 | Aeschlimann et al. |
| 2011/0071372 A1 | 3/2011 | Sloan et al. |
| 2011/0071464 A1 | 3/2011 | Palerm |
| 2011/0071465 A1 | 3/2011 | Wang et al. |
| 2011/0071765 A1 | 3/2011 | Yodfat et al. |
| 2011/0077481 A1 | 3/2011 | Say et al. |
| 2011/0077963 A1 | 3/2011 | Knudsen et al. |
| 2011/0082439 A1 | 4/2011 | Wenger et al. |
| 2011/0092788 A1 | 4/2011 | Long et al. |
| 2011/0092894 A1 | 4/2011 | Mcgill et al. |
| 2011/0098548 A1 | 4/2011 | Budiman et al. |
| 2011/0098637 A1 | 4/2011 | Hill |
| 2011/0098638 A1 | 4/2011 | Chawla et al. |
| 2011/0098674 A1 | 4/2011 | Vicente et al. |
| 2011/0101995 A1 | 5/2011 | Shah et al. |
| 2011/0105955 A1 | 5/2011 | Yudovsky et al. |
| 2011/0106011 A1 | 5/2011 | Cinar et al. |
| 2011/0106050 A1 | 5/2011 | Yodfat et al. |
| 2011/0106480 A1 | 5/2011 | Shah et al. |
| 2011/0112504 A1 | 5/2011 | Causey et al. |
| 2011/0112505 A1 | 5/2011 | Starkweather et al. |
| 2011/0112506 A1 | 5/2011 | Starkweather et al. |
| 2011/0118578 A1 | 5/2011 | Timmerman |

(56) References Cited

U.S. PATENT DOCUMENTS

| | | |
|---|---|---|
| 2011/0118662 A1 | 5/2011 | Mhatre et al. |
| 2011/0118699 A1 | 5/2011 | Yodfat et al. |
| 2011/0124996 A1 | 5/2011 | Reinke et al. |
| 2011/0124999 A1 | 5/2011 | Reggiardo et al. |
| 2011/0125085 A1 | 5/2011 | Mcgill et al. |
| 2011/0126188 A1 | 5/2011 | Bernstein et al. |
| 2011/0130716 A1 | 6/2011 | Estes et al. |
| 2011/0130746 A1 | 6/2011 | Budiman |
| 2011/0133946 A1 | 6/2011 | Kopp et al. |
| 2011/0137239 A1 | 6/2011 | Debelser et al. |
| 2011/0144586 A1 | 6/2011 | Michaud et al. |
| 2011/0144616 A1 | 6/2011 | Michaud et al. |
| 2011/0152770 A1 | 6/2011 | Diperna et al. |
| 2011/0152824 A1 | 6/2011 | Diperna et al. |
| 2011/0160654 A1 | 6/2011 | Hanson et al. |
| 2011/0160695 A1 | 6/2011 | Sigrist et al. |
| 2011/0166544 A1 | 7/2011 | Verhoef et al. |
| 2011/0166875 A1 | 7/2011 | Hayter et al. |
| 2011/0172744 A1 | 7/2011 | Davis et al. |
| 2011/0178461 A1 | 7/2011 | Chong et al. |
| 2011/0178462 A1 | 7/2011 | Moberg et al. |
| 2011/0178717 A1 | 7/2011 | Goodnow et al. |
| 2011/0184264 A1 | 7/2011 | Galasso et al. |
| 2011/0184342 A1 | 7/2011 | Pesach et al. |
| 2011/0190614 A1 | 8/2011 | Brister et al. |
| 2011/0190701 A1 | 8/2011 | Remde et al. |
| 2011/0193704 A1 | 8/2011 | Harper et al. |
| 2011/0196213 A1 | 8/2011 | Thukral et al. |
| 2011/0205065 A1 | 8/2011 | Strachan et al. |
| 2011/0208155 A1 | 8/2011 | Palerm et al. |
| 2011/0213225 A1 | 9/2011 | Bernstein et al. |
| 2011/0213306 A1 | 9/2011 | Hanson et al. |
| 2011/0256024 A1 | 10/2011 | Cole et al. |
| 2011/0257625 A1 | 10/2011 | Jasperson et al. |
| 2011/0257895 A1 | 10/2011 | Brauker et al. |
| 2011/0266999 A1 | 11/2011 | Yodfat et al. |
| 2012/0013625 A1 | 1/2012 | Blomquist et al. |
| 2012/0013802 A1 | 1/2012 | Blomquist et al. |
| 2012/0029433 A1 | 2/2012 | Michaud et al. |
| 2012/0029941 A1 | 2/2012 | Malave et al. |
| 2012/0030610 A1 | 2/2012 | DiPerna et al. |
| 2012/0041415 A1 | 2/2012 | Estes et al. |
| 2012/0053522 A1 | 3/2012 | Yodfat et al. |
| 2012/0059353 A1 | 3/2012 | Kovatchev et al. |
| 2012/0059673 A1 | 3/2012 | Cohen et al. |
| 2012/0095315 A1 | 4/2012 | Tenbarge et al. |
| 2012/0109100 A1 | 5/2012 | Estes et al. |
| 2012/0123230 A1 | 5/2012 | Brown et al. |
| 2012/0163481 A1 | 6/2012 | Ebner et al. |
| 2012/0191061 A1 | 7/2012 | Yodfat et al. |
| 2012/0191063 A1 | 7/2012 | Brauker et al. |
| 2012/0203178 A1 | 8/2012 | Tverskoy |
| 2012/0226124 A1 | 9/2012 | Blomquist |
| 2012/0232484 A1 | 9/2012 | Blomquist |
| 2012/0232485 A1 | 9/2012 | Blomquist |
| 2012/0232520 A1 | 9/2012 | Sloan et al. |
| 2012/0232521 A1 | 9/2012 | Blomquist |
| 2012/0238852 A1 | 9/2012 | Brauker et al. |
| 2012/0238854 A1 | 9/2012 | Blomquist et al. |
| 2012/0239362 A1 | 9/2012 | Blomquist |
| 2012/0245524 A1 | 9/2012 | Estes et al. |
| 2012/0265722 A1 | 10/2012 | Blomquist |
| 2012/0296269 A1 | 11/2012 | Blomquist |
| 2012/0330227 A1 | 12/2012 | Budiman et al. |
| 2013/0053816 A1 | 2/2013 | DiPerna |
| 2013/0131630 A1 | 5/2013 | Blomquist |
| 2013/0324928 A1 | 12/2013 | Kruse |
| 2013/0331790 A1 | 12/2013 | Brown et al. |
| 2013/0345625 A1 | 12/2013 | Causey, III |
| 2013/0345663 A1 | 12/2013 | Agrawal et al. |
| 2014/0005633 A1 | 1/2014 | Finan |
| 2014/0012511 A1 | 1/2014 | Mensinger et al. |
| 2014/0019396 A1 | 1/2014 | Carlsgaard et al. |
| 2014/0066890 A1 | 3/2014 | Sloan et al. |
| 2014/0074059 A1 | 3/2014 | Howell et al. |
| 2014/0137641 A1 | 5/2014 | Brown |
| 2014/0171772 A1 | 6/2014 | Blomquist |
| 2014/0273042 A1 | 9/2014 | Saint |
| 2014/0275419 A1 | 9/2014 | Ward et al. |
| 2014/0276420 A1 | 9/2014 | Rosinko |
| 2014/0276531 A1 | 9/2014 | Walsh |
| 2014/0276553 A1 | 9/2014 | Rosinko |
| 2014/0276556 A1 | 9/2014 | Saint et al. |
| 2014/0276570 A1 | 9/2014 | Saint |
| 2014/0276574 A1 | 9/2014 | Saint |
| 2014/0350371 A1 | 11/2014 | Blomquist et al. |
| 2014/0378898 A1 | 12/2014 | Rosinko |
| 2015/0045770 A1 | 2/2015 | DeBelser et al. |
| 2015/0073337 A1 | 3/2015 | Saint et al. |
| 2015/0182693 A1 | 7/2015 | Rosinko |
| 2015/0182695 A1 | 7/2015 | Rosinko |
| 2015/0217044 A1 | 8/2015 | Blomquist |
| 2015/0314062 A1 | 11/2015 | Blomquist et al. |
| 2016/0030669 A1 | 2/2016 | Harris et al. |
| 2016/0082188 A1 | 3/2016 | Blomquist et al. |
| 2016/0199571 A1 | 7/2016 | Rosinko et al. |
| 2016/0228041 A1 | 8/2016 | Heller et al. |
| 2017/0043085 A1 | 2/2017 | Rosinko |
| 2017/0182248 A1 | 6/2017 | Rosinko |

FOREIGN PATENT DOCUMENTS

| | | |
|---|---|---|
| DE | 19819407 | 11/1999 |
| DE | 10121317 | 11/2002 |
| DE | 10352456 | 7/2005 |
| EP | 1102194 | 5/2001 |
| EP | 1571582 | 9/2005 |
| JP | 2006034323 | 2/2006 |
| WO | WO0045696 | 8/2000 |
| WO | WO0074753 | 12/2000 |
| WO | WO0152727 | 7/2001 |
| WO | WO02062212 | 8/2002 |
| WO | WO03082091 | 10/2003 |
| WO | WO2005046559 | 5/2005 |
| WO | WO06061169 | 6/2006 |
| WO | WO2006127841 | 11/2006 |
| WO | WO2007000425 | 1/2007 |
| WO | WO2007056592 | 5/2007 |
| WO | WO2007089537 | 8/2007 |
| WO | WO07149533 | 12/2007 |
| WO | WO2008048556 | 4/2008 |
| WO | WO2008048582 | 4/2008 |
| WO | WO2008048583 | 4/2008 |
| WO | WO2008048584 | 4/2008 |
| WO | WO2008048585 | 4/2008 |
| WO | WO2008048586 | 4/2008 |
| WO | WO2008048587 | 4/2008 |
| WO | WO2008091320 | 7/2008 |
| WO | WO2008103175 | 8/2008 |
| WO | WO2008112078 | 9/2008 |
| WO | WO2008144693 | 11/2008 |
| WO | WO2008144695 | 11/2008 |
| WO | WO2008144697 | 11/2008 |
| WO | WO2008144698 | 11/2008 |
| WO | WO2008153689 | 12/2008 |
| WO | WO2008153819 | 12/2008 |
| WO | WO2009016636 | 2/2009 |
| WO | WO2009032399 | 3/2009 |
| WO | WO 2009032400 | 3/2009 |
| WO | WO2009032400 | 3/2009 |
| WO | WO2009035759 | 3/2009 |
| WO | WO09089028 | 7/2009 |
| WO | WO2009088983 | 7/2009 |
| WO | WO2009089029 | 7/2009 |
| WO | WO2011068648 | 6/2011 |
| WO | WO2013016363 | 1/2013 |
| WO | WO2013184896 | 12/2013 |

OTHER PUBLICATIONS

Canadian Office Action for Canadian Application No. 2,782,673 dated Sep. 10, 2013.

(56) References Cited

OTHER PUBLICATIONS

European Office Action for European Application No. 08779626.4 dated May 25, 2010.
Deltec Cozmo, Personalized Insulin Pump. Starting Guide, Smith Medical MD, Inc. online. http://web.archive.org/web/20041207133223/http://www.cozmore.com/Library/upload/starting_guide_032004.pdf, Dec. 7, 2004. pp. 1-83.
International Search Report and Written Opinion for International Application No. PCT/US2008/006449 dated Oct. 10, 2008.
International Search Report and Written Opinion for International Application No. PCT/US2008/006801 dated Oct. 30, 2008.
Wikipedia define "basal rate" printed on Jun. 12, 2009.
Compare Insulin Pump for Diabetes, www.diabetesnet.com printed on Jun. 18, 2009.
Walsh, et al., "Title Page, Citation page and table of contents" Pumping Insulin: Everything You need for Success on a Smart Insulin Pump. Torrey Pines Press, San Diego 2006.
European Office Action for European Application No. 08767734.6 dated Apr. 7, 2010, 6 pages.
Walsh et al., Select and Test Your Correction Factor Pumping Insulin Fourth Edition, Chapter 13, (2006) 29 pages.
Chinese Office Action for Chinese Application No. 201080063326.9 dated Jan. 27, 2014. English Translation not provided.
Application and File History for U.S. Appl. No. 14/187,414, filed Feb. 24, 2014, inventor Blomquist.
Application and File History for U.S. Appl. No. 11/753,420, filed May 24, 2007, inventor Blomquist.
Application and File History for U.S. Appl. No. 14/962,635, filed Dec. 8, 2015, inventors Blomquist et al.
Application and File History for U.S. Appl. No. 14/813,699, filed Jul. 30, 2015, inventors Harris et al.
Application and File History for U.S. Appl. No. 15/394,066, filed Dec. 29, 2016, inventors Rosinko.
Application and File History for U.S. Appl. No. 12/774,991, filed May 6, 2010, inventor Blomquist.
Application and File History for U.S. Appl. No. 13/530,404, filed Jun. 22, 2012, inventor Blomquist.
Application and File History for U.S. Appl. No. 14/684,495, filed Apr. 13, 2015, inventor Blomquist.
Application and File History for U.S. Appl. No. 11/685,617, filed Mar. 13, 2007, inventors Blomquist et al.
International Search Report and Written Opinion for International Application No. PCT/US200900034 dated May 27, 2009.
Walsh, "Diabetes Technology Concept 1: Super Bolus" Online. http://www.diabetesnet.com/diabetes_technology/super_bolus.php> Sep. 17, 2007, (3 pages).
International Preliminary Report and Written Opinion for International Application No. PCT/US2010/056233 date of issuance of this report is Jun. 5, 2012.
PCT Search Report dated Aug. 31, 2011 for PCT Application No. PCT/US2010/056233 filed Nov. 10, 2010.
International Search Report and Written Opinion for International Application No. PCT/US2007/024423 dated May 19, 2008.
International Search Report and Written Opinion for International Application No. PCT/US2009/000106 dated May 13, 2009.
Plougmann et al., "DiasNet-a diabetes advisory system for communication and education via the internet", International Journal of Medical Informatics, vol. 26. pp. 319-330 (2001).
Wilinska et al., "Insulin Kinetics in Type-1 Diabetes: Continuous and Bolus Delivery of Reapid Acting Insulin>" IEEE Transactions on Bopmedical Engineering vol. 52. No. 1, pp. 3-12. Jan. 2005.

Bott et al., "Impact of Smoking on the Metabolic Action of Subcutaneous Regular Insulin in Type 2 Diabetic Patients" Horm. Metab. Res., vol. 37, pp. 445-449 (2005).
Puckett et al., Am. J. Physiol. vol. 269, p. E1115-E1124, 1995 "A Model for Multiple Subcutaneous Insulin Injections Developed from Individual Diabetic Patient Data".
Wach et al., Med & Biol. Eng & comput., vol. 33, p. 18-23, 1995. "Numerical Approximation of Mathematical Model for Absorption of Subcutaneously Injected Insulin".
Lehmann et al., Artificial Intelligence in Medicine, vol. 6, p. 137-160,1994. Combining rule-based reasoning and mathematical modeling in diabetes care.
Chase et al., The Use of Insulin Pumps With Meal Bolus Alarms in Children With Type 1 Diabetes to Improve Glycemic Control, Diabetes Carem vol. 29, No. 5. May 2006. 1012-1015.
International Search Report and Written Opinion for International Application No. PCT/US2007/022050 dated Mar. 7, 2008.
International Search Report and Written Opinion for International Application No. PCT/US09/00107 dated May 4, 2009,.
Search Report and Written Opinion dated May 7, 2014 for PCT Application No. PCT/US2014/021318.
Stapel, Elizabeth, "Converting Between Decimals, Fractions, and Percents", Purplemath. 2006, http://www.purplemath.com/modules/percents2.htm.
International Search Report and Written Opinion for International Application No. PCT/US2007/022046 dated Mar. 7, 2008.
Trajanoski et al., Pharmacokinetic Model for the Absorption of Subcutaneoutsly Injected Soluble Insulin and Monomeric Insulin Analogues. Biomedizinische Technik,. vol. 38 No. 9. Sep. 1, 1993.
Hildebrandt, Subcutaneous Absorption of Insulin in Insulin- Dependent Diabetic patients. Influence of Species Physico-Chemical properties of Insulin and Physiological factors. Danish Medical Bulletin. Aug. 1991.
International Search Report and Written Opinion for International Application No. PCT/US2007/022004 dated Oct. 9, 2008.
International Search Report and Written Opinion for International Application No. PCT/US2007/022047 dated Mar. 7, 2008.
International Search Report and Written Opinion for International Application No. PCT/US2007/022048 dated Mar. 7, 2008.
International Search Report and Written Opinion for International Application No. PCT/US2007/022049 dated Mar. 7, 2008.
International Search Report and Written Opinion for International Application No. PCT/US2007/022051 dated Mar. 7, 2008.
International Search Report and Written Opinion for International Application No. PCT/US2007/022052 dated May 11, 2007.
European Office Action from European Application No. 07852760.3 dated Aug. 11, 2010.
Written Opinion and International Search Report for International Application No. PCT/US2008/002536 dated Sep. 4, 2008.
Application and File History for U.S. Appl. No. 14/455,508, filed Aug. 8, 2014, inventors Blomquist et al.
Application and File History for U.S. Appl. No. 13/842,005, filed Mar. 15, 2013, inventors Saint et al.
European Search Report for European U.S. Appl. No. 15/168,432 dated completed Sep. 1, 2015 and dated Sep. 8, 2015.
Application and File History for U.S. Appl. No. 13/800,453, filed Mar. 13, 2013, inventors Rosinko et al.
International Search Report and Written Opinion for International Application No. PCT/US2014/021109 dated Jun. 5, 2014.
International Search Report and Written Opinion for International Application No. PCT/US2015/042881 dated Nov. 11, 2015.

\* cited by examiner

BASAL RATE TESTING USING FREQUENT BLOOD GLUCOSE INPUT

RELATED APPLICATION

This application is a continuation of application Ser. No. 11/685,617 filed Mar. 13, 2007, which is hereby fully incorporated herein by reference.

TECHNICAL FIELD

The field generally relates to patient insulin management devices and, in particular, but not by way of limitation, to systems, devices and methods for adjusting insulin therapy.

BACKGROUND

People who suffer from diabetes require insulin to keep their blood glucose level as close as possible to normal levels. It is essential for people with diabetes to manage their blood glucose level to within a normal range. Complications from diabetes can include heart disease (cardiovascular disease), blindness (retinopathy), nerve damage (neuropathy), and kidney damage (nephropathy). Insulin is a hormone that reduces the level of blood glucose in the body. Normally, insulin is produced by beta cells in the pancreas. In non-diabetic people, the beta cells release insulin to satisfy two types of insulin needs. The first type is a low-level of background insulin that is released throughout the day. The second type is a quick release of a higher-level of insulin in response to eating. Insulin therapy replaces or supplements insulin produced by the pancreas.

Conventional insulin therapy typically involves one or two injections a day. The low number of injections has the disadvantage of allowing larger variations in a person's insulin levels. Some people with diabetes manage their blood glucose level with multiple daily injections (MDI). MDI may involve more than three injections a day and four or more blood glucose tests a day. MDI offers better control than conventional therapy. However, insulin injections are inconvenient and require a diabetic person to track the insulin doses, the amount of carbohydrates eaten, and their blood glucose levels among other information critical to control.

Blood glucose (BG) management devices help a diabetic person manage their blood glucose. For example, an insulin pump is a BG management device that provides insulin throughout the day. A glucose monitor (GM) or meter is a BG management device that measures blood glucose levels. Some GMs require a finger-stick to acquire a sample of blood that is applied to a test strip to get a blood glucose reading. Some GMs are able to provide continuous monitoring of blood glucose. Other BG management devices include computers running software to help a diabetic person manage insulin therapy. However, most BG management devices are limited in the control over blood glucose that they offer.

SUMMARY

This document discusses, among other things, devices and methods for managing insulin therapy. A device example includes a user interface configured to generate an electrical signal to start a basal insulin rate test when prompted by a user, an input configured to receive sampled blood glucose data of a patient that is obtained during a specified time duration, including a time duration during delivery of insulin according to a specified basal insulin rate pattern, and a controller communicatively coupled to the input and the user interface. The controller includes an insulin calculation module configured for determining at least one of an amount of basal insulin over-delivered and an amount of basal insulin under-delivered during the basal insulin rate test in trying to meet a target blood glucose baseline.

A method example includes receiving a user prompt in a blood glucose (BG) management device to start a basal insulin rate test, receiving sampled blood glucose data that is obtained during a specified duration of time when insulin is delivered according to a specified basal insulin rate pattern, and determining at least one of an amount of basal insulin over-delivered and an amount of basal insulin under-delivered in trying to meet a target blood glucose baseline during the basal insulin rate test using the BG management device.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

Figure 1:
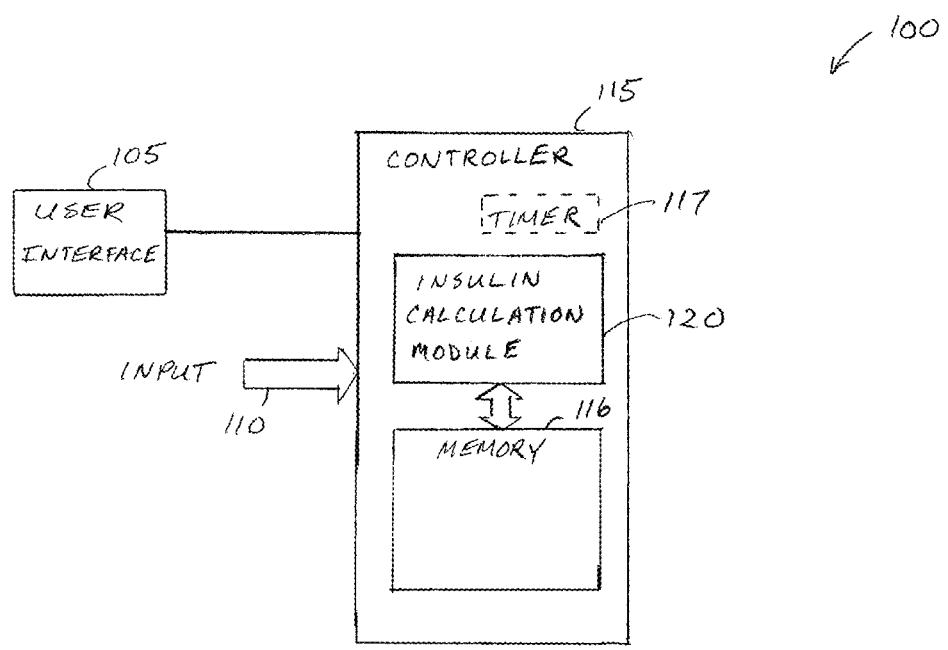
FIG. 1 is a block diagram of portions of a BG management device.

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

It is important for a diabetic person to be treated with the proper amount of insulin. As discussed previously, high blood sugar can lead to serious complications. Conversely, a person with low blood sugar can develop hypoglycemia. Ideally, insulin therapy mimics the way the body works. An insulin pump is one way to mimic the body's insulin production. An insulin pump can provide a background or basal infusion of insulin throughout the day and provide a quick release or bolus of insulin when carbohydrates are eaten. If a person develops high blood sugar, a correction bolus can be delivered by the pump to correct it. While insulin pumps improve convenience and flexibility for a diabetic person, they can be sophisticated devices. Some insulin pumps can be difficult to program. Proper use of an insulin pump requires a user to go through a learning curve to properly use and program the pump.

Basal rate refers to a type of twenty-four hour background infusion of insulin by an insulin pump that mimics the continuous background release of insulin from a normal pancreas. It is the rate of insulin delivery the patient normally needs independent of the consumption of meals. The basal rate is typically specified in insulin units per hour (u/hr). Typically, a basal rate for a pump is initially programmed by a clinician based on a total daily dose (TDD) of insulin for a diabetic person. The clinician may determine TDD based on many factors including the type of diabetes of the patient and the patient's weight, age, and level of fitness. The amount of basal insulin is typically determined to be a percentage of TDD, such as 40%, 50%, or 60% for example. The total daily dose is then divided by 24 to obtain an average basal rate. For example, if a patient's TDD is determined to be 40 units of insulin, and 50% of the TDD is used for basal delivery, the average basal rate is 20 units/24 hours or 0.83 u/hr.

Many insulin pump users may use three or more different basal rates during the course of a day. Basal rates can be adjusted to change delivery every few minutes (e.g., 20-30 minutes) by increments as small as 0.05 u/hr to better track changes in demand, such as from an increase typically needed before dawn or a decrease needed during long active periods. Insulin pump users may use different basal rates for overnight, for breakfast to mid-afternoon, and for mid-afternoon to bedtime. Appropriate basal rates vary from person to person, may be different for a person at various times of the day, and may change for a person over time. Inappropriate basal rate settings may result in low blood glucose levels overnight or high blood glucose levels in the morning. An insulin pump user may go through several iterations of trial and error before finding appropriate basal rates. Because a patient's basal insulin needs may change over time, such as with weight change or with a change in fitness level, basal rate testing may be performed periodically to ensure that an appropriate basal rate is being delivered by an insulin pump. Blood glucose (BG) management devices are more valuable to a diabetic person if the device conveniently assists them in determining their appropriate basal rate or rates.

Apparatus Embodiments

FIG. 1 is a block diagram of portions of a BG management device 100. Examples of a BG management device 100 include, among other devices, an insulin pump, a blood glucose monitor (GM) or meter, and a computing device running software to assist a diabetic patient in managing insulin therapy. Examples of a computing device include, among other things, a personal computer or a personal data assistant (PDA).

The BG management device 100 includes a user interface 105, an input 110, and a controller 115 communicatively coupled to the input 110 and the user interface 105. The controller 115 can be implemented using hardware circuits, firmware, software or any combination of hardware, firmware and software. Examples, include a microcontroller, a logical state machine, and a processor such as a microprocessor, application specific integrated circuit (ASIC), or other type of processor.

The user interface 105 generates an electrical signal to begin a basal rate test when prompted by a user. The user interface 105 may include a pushbutton, keypad, or a computer mouse. The user interface 105 may include a display operatively coupled to the controller 115 to provide patient or user instructions for the basal rate test. Examples of instructions include, among other things, instructing the patient not to eat during the test, to maintain a normal activity level, and not to administer an insulin correction bolus during the test. The display may include a touchscreen. The user of the device may be a clinician, caregiver, or a diabetic patient. The user prompts the BG management device 100 using the user interface 105 to begin a basal rate test. The basal rate test assists the user in determining one or more appropriate basal rates.

As part of a basal rate test, the patient receives insulin according to a specified basal rate pattern or profile. If the BG management device 100 includes an insulin pump, the basal insulin may be delivered using the BG management device 100. If the BG management device 100 does not include an insulin pump, the basal insulin may be delivered using a separate device that includes an insulin pump.

If the BG management device 100 includes an insulin pump, the BG management device 100 may further include a memory 116 to store at least one basal rate pattern. The controller 115 may display instructions for the user to enter one or more basal rates to be delivered according to time of day. For example, the BG management device 100 may allow the user to enter basal rate values in 0.05 u/hr increments, and to enter time in increments of one-half hour throughout the day. In some embodiments, the BG management device 100 stores different basal rate patterns according to different segments of the day, such as early in the day, late in the day, and overnight for example. In some embodiments, the input 110 may include a communication port and a basal rate pattern may be loaded from a second device into memory 116.

The input 110 is configured to receive sampled blood glucose data of the patient as part of the basal rate test. The blood glucose data provides an indication of the concentration level of the patient's blood sugar and the data may be obtained from blood directly or from insterstitial fluid. The blood glucose data is obtained during a specified time duration. The specified time duration includes a time when insulin is delivered according to a specified basal rate pattern, but may include a time prior or after the delivery of insulin as well. The configuration of the input 110 may depend on the type of BG management device 100. If the BG management device 100 is an insulin pump, the input 110 may be coupled to a GM included in the pump or the input 110 may include a communication port to receive the blood glucose data from a second device. The second device may include a GM or the second device may receive the blood glucose data from a third device. In some embodiments, the input 110 is coupled to the user interface 105, and the user may manually input the data into the pump through a keypad or keyboard included in the user interface.

The controller 115 includes an insulin calculation module 120. Modules can be software, hardware, firmware or any combination of software, hardware, and firmware. Multiple functions can be performed in one or more modules. The insulin calculation module 120 determines at least one of an amount of basal insulin over-delivered and an amount of basal insulin under-delivered during the basal insulin rate test in trying to meet a target blood glucose baseline.

Figure 2:
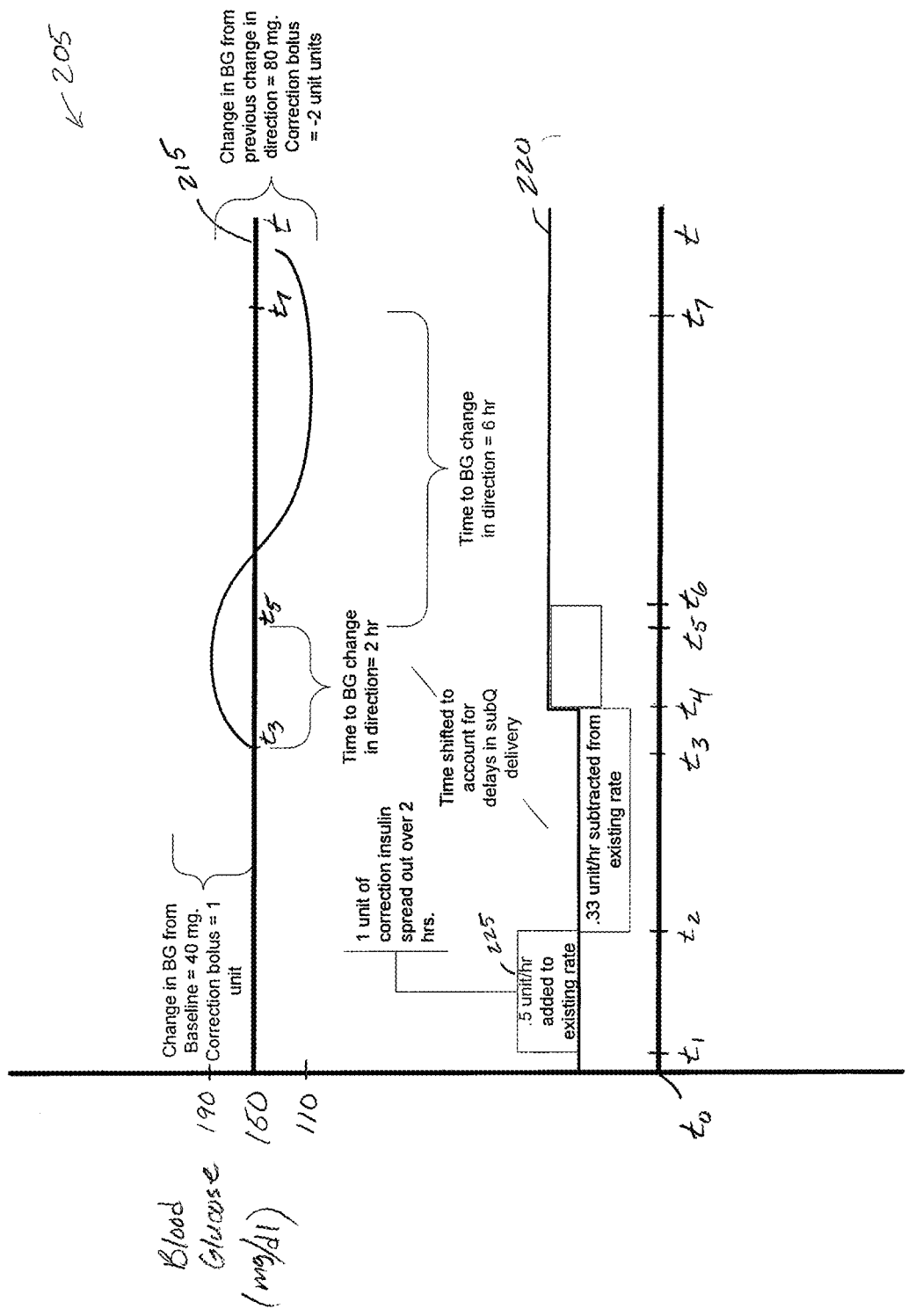
FIG. 2 shows example illustrations of a blood glucose concentration graph and a basal rate pattern.

FIG. 2 shows example illustrations (not real data) of a blood glucose concentration graph 205 and a basal rate pattern 220 or profile during a basal rate test. Assume, as shown in the blood glucose concentration graph 205, that the patient's target blood glucose baseline 215 is 150 mg/dl (milligrams per deciliter) and that this is the patient's blood glucose concentration level before the basal rate test. Basal insulin is being delivered according to a basal rate pattern 220. At time $t_0$, the user elects to begin a basal rate test. User instructions for the basal rate test may be provided. The blood glucose concentration is determined from blood glucose data received into the input 110 during the basal rate test. The basal rate test may run over several hours, e.g., six to eight hours. In some embodiments, the blood glucose data may be stored in memory for processing. In some embodiments, the blood glucose data may be processed by the insulin calculation module 120 as it is received.

If the patient's blood glucose level remains at the target blood glucose baseline 215 or within a specified range of the target blood glucose baseline 215, the basal profile is appropriate. If the patient's blood glucose level rises above the target blood glucose baseline 215 or rises above a specified range of the target blood glucose baseline 215, the basal rate is too low and there was an under-delivery of basal insulin. If the patient's blood glucose level falls below the target blood glucose baseline 215 or falls below a specified range of the target blood glucose baseline 215, the basal rate is too high and there was an over-delivery of basal insulin.

In the example in FIG. 2, the patient's blood glucose begins to rise at time $t_3$. The change in the blood glucose from the baseline reaches 190 mg/dl, or an increase of 40 mg/dl. At time $t_4$, the basal rate pattern 220 includes an increase in basal rate. The blood glucose level of the patient begins to change direction, here a decrease, at time $t_5$. The time duration from the increase at $t_3$ to the change in direction at $t_5$ is about two hours in this example. The blood glucose level of the patient eventually falls to 110 mg/dl, or a total decrease of 80 mg/dl. At time $t_7$, the blood glucose level of the patient begins to again change direction. This time the change in direction is an increase in blood glucose concentration. The time duration from the decrease at $t_5$ to the change in direction at $t_7$ is about six hours.

In some embodiments, the insulin calculation module 120 is configured to determine the over-delivered amount or the under-delivered amount of basal insulin using a correction factor of the patient and a variance of a blood glucose level from the target blood glucose baseline 215. A correction factor refers to the amount of drop in blood glucose concentration of the patient for one unit of insulin. In FIG. 2, the 40 mg/dl increase corresponds to an under-delivery of basal insulin. The under-delivery may be due to the basal rate being too low or due to an increased demand from the patient during that time of day. The 80 mg/dl decrease corresponds to an over-delivery of basal insulin.

To calculate the amount under-delivered, the insulin calculation module 120 divides the increase in blood glucose level (+40 mg/dl) by the correction factor of the patient to determine the amount of insulin required to lower the blood glucose level to the target blood glucose baseline 215. This is the amount of insulin that was under-delivered to the patient during the basal rate test. Assume in the example of FIG. 2 that the patient's correction factor is one unit per 40 mg/dl. In this case, a correction bolus of one unit of insulin would decrease the patient's blood glucose level to the blood glucose baseline. To calculate the amount of insulin over-delivered, the insulin calculation module 120 divides the decrease in blood glucose level (−80 mg/dl) by the correction factor of the patient (1 u per 40 mg/dl). This corresponds to a correction bolus of −2 units of insulin, i.e., the amount of insulin delivered needs to be reduced by 2 units of insulin.

The under-delivered or over-delivered amount can be used to recommend changes to the basal rate pattern. In the example of FIG. 2, the insulin calculation module 120 may determine that the existing basal rate pattern 220 needs to be increased at some point by one unit of insulin to address the 40 mg/dl increase and decreased at some point by 2 units of insulin to address the 80 mg/dl decrease.

The BG management device 100 is more valuable if recommended changes anticipate an under-delivery or over-delivery. However, anticipating when to change the basal rate is complicated by a delay, or a lag time, in insulin uptake before the insulin becomes effective. Another complication is that the lag time may be different for glucose levels measured using blood and glucose levels measured using interstitial fluid. Measuring blood glucose concentration using the interstitial fluid may make the uptake appear to have additional lag time. In some embodiments, the insulin calculation module 120 recommends a change in a basal rate that precedes any actual times of under-delivery or over-delivery by a time duration that compensates for a lag time associated with the subcutaneous insulin delivery and with the glucose measurement method.

In some embodiments, in addition to the uptake lag time, the insulin calculation module 120 uses the time from a beginning of a change in the blood glucose level to a change in direction of the blood glucose data values to determine a recommended change to the basal insulin rate pattern 220. In the example of FIG. 2, it is determined that one unit of insulin is needed to correct the under-delivery of insulin resulting in the 40 mg/dl increase in blood glucose level. The increase began at $t_3$ and a change in direction occurred two hours later at $t_5$. The insulin calculation module 120 may recommend a change that includes adding one unit of insulin to the basal rate pattern 220 and spreading the delivery out over two hours corresponding to the change in direction time, i.e., a rate of 0.5 u/hr. This shown by the basal rate increase 225 of 0.5 u/hr for two hours over time $t_1$ to $t_2$. The time $t_1$ is shifted earlier than the time of the increase at $t_3$ by a time duration to compensate for a delay in the insulin uptake so that the insulin may act on the blood glucose.

Also in FIG. 2, an over-delivery of 2 units of insulin resulted in an 80 mg/dl increase in blood glucose level. The decrease began at $t_5$ and a change in direction occurred six hours later at $t_7$. The insulin calculation module 120 may recommend a change that includes subtracting two units of insulin from the basal rate pattern 220 over six hours at a rate of 0.33 u/hr. This shown by the basal rate decrease 230 of 0.33 u/hr for six hours over time $t_2$ to $t_6$. The time $t_2$ is early enough to compensate for the delay in insulin uptake.

The lag time for insulin uptake may depend on several factors. In some embodiments, the insulin calculation module 120 determines a time duration to compensate for such a time lag using the type of insulin delivered. Some insulin types have a faster uptake than other types, and the insulin calculation module 120 may use a table stored in a memory of the BG management device to correlate a time duration to an insulin type. In some embodiments, the insulin calculation module 120 calculates the compensating time duration using an activity level of the patient and/or the fitness level of the patient. In some embodiments, the compensating time lag is pre-determined from clinical studies and is stored in a memory for use by the insulin calculation module 120.

In some embodiments, the insulin calculation module 120 may adjust the correction factor before determining an amount of insulin under or over-delivered. In certain embodiments, the insulin calculation module 120 may use a correction factor multiplier to adjust the correction factor when determining the amount of insulin under or overdelivered, and consequently adjusting the amount of insulin in any recommended changes to the basal rate pattern 220. For example, assume as in FIG. 2 that the patient's correction factor is one unit per 40 mg/dl. If the correction factor multiplier is 1.3, the insulin calculation module uses a correction factor of one unit per 52 mg/dl [(1.3)(40 mg/dl/unit)]. For the 40 mg/dl increase in FIG. 2, the insulin calculation module 120 divides the increase in blood glucose level (40 mg/dl) by the correction factor of the patient (1 u per 52 mg/dl). This corresponds to a correction bolus of 0.77 units [(40)/(52)] of insulin. The insulin calculation module 120 may recommend adding 0.39 u/hr for two hours to the basal rate pattern.

Using a correction factor multiplier results in a lower amount of basal insulin allowing adjustments to be made more safely made. This may give a user more confidence in using the recommended changes to the basal rate pattern 220. The 80 mg/dl decrease corresponds to a correction bolus of 1.54 units of insulin. The insulin calculation module 120 may recommend subtracting 0.26 u/hr for six hours to the basal rate pattern. The controller 115 may store the correction factor multiplier in a memory. The correction factor multiplier may be manually set or programmed by a clinician. The clinician may set the correction factor multiplier to a value that accords to a level of confidence or comfort to the clinician in the recommended changes to the basal rate pattern 220.

In some embodiments, if the blood glucose data received during the basal rate test indicates that the blood glucose level of the patient is outside of a specified range of blood glucose levels, the controller 115 cancels the basal insulin rate test. If the blood glucose level is above the range, the controller 115 may recommend a correction bolus to be taken by the patient. The insulin calculation module 120 calculates the amount of insulin in the correction bolus by dividing the blood glucose concentration by the specified correction factor for the patient.

If the blood glucose level is below the range, the controller 115 may recommend an amount of carbohydrates to be eaten by the patient. The insulin calculation module 120 calculates the amount of carbohydrates using a correction factor specified for the patient and a carbohydrate ratio specified for the patient. A carbohydrate ratio refers to the amount of carbohydrates reduced, or covered, by a unit of insulin.

For example, assume that at the beginning of a basal rate test, the blood glucose level of a patient is 40 mg/dl below the specified range and the specified correction factor is 1 unit per 80 mg/dl. The insulin calculation module 120 determines that −0.5 units of insulin (−40/80) are required to bring the blood glucose level back within the specified range. Negative insulin cannot be delivered so this corresponds to a requirement for carbohydrates. Assume that the carbohydrate ratio of the patient is 20 grams of carbohydrates per unit of insulin (20 g/u). The insulin calculation module 120 multiplies the amount of insulin by the carbohydrate ratio to determine that the patient should eat 10 grams of carbohydrates [(0.5)(20)]. The insulin calculation module 120 may take into account additional factors such as the health status of the patient and the activity level of the patient in recommending the carbohydrate amount. In some embodiments, if the blood glucose of the patient is outside the specified range of blood glucose levels, the controller 115 suspends the start of the basal insulin rate test until the blood glucose of the patient is within the specified range of blood glucose levels.

As discussed previously, appropriate basal rates may differ for a patient throughout the course of a day. The BG management device 100 may include a timer circuit 117 operatively coupled to the controller 115. The controller 115 displays user instructions to execute a basal rate test at one or more specified times during a day. In some embodiments, controller 115 displays user instructions to run the basal insulin rate test on multiple days. The controller 115 may prompt the user to run the test during substantially the same time on the multiple days. This may result in more appropriate basal delivery rates being used at different times during the day.

It is often difficult to maintain a stable blood glucose target value overnight because the correction factor varies as a function of time. In order to stabilize the glucose value at a target blood glucose value, the basal rate may often be adjusted during overnight periods to compensate for changes in the correction factor. An insulin pump user may go through several iterations of trial and error while attempting to find appropriate overnight basal rates. A trial and error method may result in less than optimal control of overnight blood glucose level.

According to some embodiments, the BG management device 100 automatically executes a basal rate test during a period when food intake is restricted, such as overnight for example. The basal rate test may start a specified time after a user prompts the BG management device 100 to execute the basal rate test. For example, if the period is overnight, the user prompt may start a timer circuit and the controller 115 may initiate the overnight basal rate test when a time duration expires. The insulin calculation module 120 automatically determines one or more basal rates for a basal rate profile using a basal rate calibration and verification technique. The basal blood glucose value g can be approximated by $$g(t) \approx c(t)b(t-\tau), \qquad (1)$$

where c(t) is the basal correction factor, b(t) is the basal insulin rate, and τ is the delay or lag time associated with the uptake of a subcutaneous infusion of insulin. Food consumption and exercise are assumed to be negligible during the period of the test.

The insulin calculation module 120 may perform a rapid calibration that can be executed during a period as short as two time periods, such as two nights for example. The correction factor c(t) may vary as a function of time. To determine c(t), blood glucose data values $g_1(t)$ and basal insulin delivery rates $b_1(t)$ are recorded periodically throughout a first observation period. Rewriting Equation (1) to solve for c(t) for the first period yields $$c_1(t) = \frac{g_1(t)}{b_1(t-\tau_1)}. \qquad (2)$$

The delay for insulin uptake $\tau_1$ can be an assumed value based on current estimates from clinical studies that use that type of insulin, or can be determined on a per patient basis using stochastic or deterministic time series analysis of prior or current basal test data. The time series analysis of the blood glucose data values may be performed under pulse function, step function, or continuous changes in insulin delivery. The time-dependent changes in insulin delivery may be present in the user's current basal profile or the user may be prompted to create a time-dependent change by the insulin calculation module. The stochastic or deterministic time series analysis can be performed on blood glucose data obtained from previous calibration or observation periods, such as previous nights for example. Thus, the delay for insulin uptake may be determined using blood glucose data obtained prior to the basal rate test.

A desired target blood glucose value $g_t(t)$ may be a constant or a function of time. Equation (1) can be written as $$g_t(t) \cong c_1(t)b_t(t-\tau_1), \quad (3)$$

where $c_1(t)$ is the correction factor determined from the first period of data values from Equation (2). Solving equation (3) for a controlling basal insulin rate $b_t(t)$ that achieves the desired $g_t(t)$ yields $$b_t(t) = \frac{g_t(t+\tau_1)}{c_1(t+\tau_1)}. \quad (4)$$

It is assumed that the correction factor $c(t)$ is a periodic function that repeats on a twenty four hour cycle, and that $c(t)$ determined from data and basal rates during the first period of reduced food intake will be similar on subsequent periods twenty-four hours later.

During the second period of observation, blood glucose data values $g_2(t)$ and basal rates $b_2(t)$ are again recorded periodically. Ideally $g_2(t)=g_t(t)$, but in reality $g_2(t)=g_t(t)+\varepsilon(t)$, where $\varepsilon(t)$ is the residual deviation from the target blood glucose value. Thus, Equation (1) can be written as $$g_t(t)+\varepsilon(t)=c_1(t)b_1(t-\tau_1). \quad (5)$$

Assuming that $\varepsilon(t)$ is primarily due to the error in the estimate of $\tau_1$, Equation (5) can be rewritten as $$g_t(t)+\varepsilon(t)=c_1(t)b_{t1}(t-(\tau_1-\delta)), \quad (6)$$

where $\delta$ is the error in the delay estimate. Combining Equations 5 and 6 gives $$\varepsilon(t)=c_1(t)[b_t(t-\tau_1)-b_t(t-(\tau_1-\delta))]. \quad (7)$$

Curve fitting or other standard minimization techniques can be used to determine the most appropriate estimate of $\delta$ to satisfy Equation (7). Once $\delta$ is determined, the control estimate for the basal insulin delivery rate or rates $b_t(t)$ that achieves the desired blood glucose target $g_t(t)$ can be written as $$b_t(t) = \frac{g_t(t+\tau_2)}{c_1(t+\tau_2)}, \quad (8)$$

where $\tau_2=\tau_1-\delta$. The insulin calculation module may then recommend changes to the t basal rate pattern using $b_t(t)$.

The rapid calibration technique is a method to quickly achieve improved control over blood glucose level. In some embodiments, the insulin calculation module 120 executes a basal rate test that uses a generalized calibration technique to achieve more accurate estimates of $b_t(t)$. The generalized calibration method uses least squares estimation techniques with at least two periods of observing blood glucose data and basal insulin delivery rates. Referring back to Equation (1) and with g(t) and b(t) measured over several periods, $\tau$ and c(t) can be estimated by curve fitting with a finite order polynomial or an orthogonal series approximation such as a Fourier series approximation for example. The resulting estimate of $b_t(t)$ is calculated using Equation 3 with $\tau$ and c(t) estimated from the curve fit results.

Figure 3:
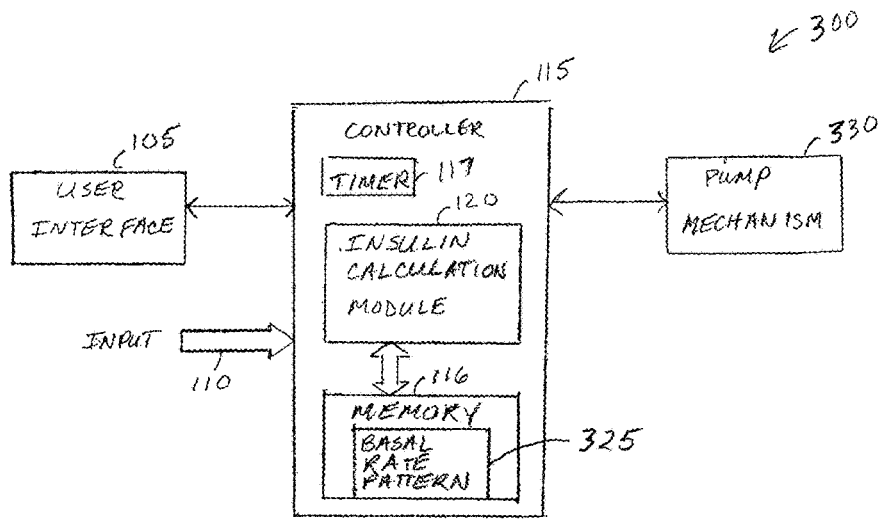
FIG. 3 is a block diagram of portions of an example of a BG management device that includes a pump mechanism.

According to some embodiments, the BG management device includes an insulin pump. FIG. 3 is a block diagram of portions of an example of a BG management device 300 that includes a pump mechanism 330 to deliver insulin to the patient. The pump mechanism 330 is operatively coupled to the controller 115. The controller 115 may track the amount of insulin delivered via the pump mechanism 330. The BG management device 300 includes a memory 116 operatively coupled to the controller 115 to store one or more basal rate patterns 325. The BG management device delivers basal insulin according to the basal rate patterns. The BG management device 300 also may deliver insulin through boluses such as a correction bolus or a carbohydrate bolus. In some embodiments, the BG management device 300 has a timer circuit 117 that includes a real time clock coupled to the controller 115. The controller 115 is configured to vary a basal rate of insulin delivery by a time of day according to a basal rate pattern.

In some embodiments, the insulin calculation module 120 is able to keep track of the amount of active insulin in the patient. This is sometimes referred to as insulin on board (IOB). To track the amount of active insulin, the controller 115 uses the amount of insulin delivered, the time that elapsed since delivery of insulin and a duration of how long the insulin is active in the blood. The duration may be determined using kinetic action, which is the time it takes for insulin to disappear from the blood, or the duration of insulin action (DIA), which is how long the insulin lowers blood glucose. In some embodiments, the controller 115 cancels a basal rate test if the insulin calculation module 120 determines that the active insulin amount is above a specified threshold insulin amount. This minimizes the risk of IOB confounding the results of the basal rate test.

In some embodiments, the controller 115 cancels the basal insulin rate test if the controller 115 determines that an insulin bolus dose, such as a correction insulin bolus or a carbohydrate insulin bolus, is delivered during the basal insulin rate test. In some embodiments, if the user enables an insulin bolus delivery, the controller 115 displays a warning that the basal insulin test will be canceled if the user elects to proceed with delivery of the insulin bolus dose.

Figure 4:
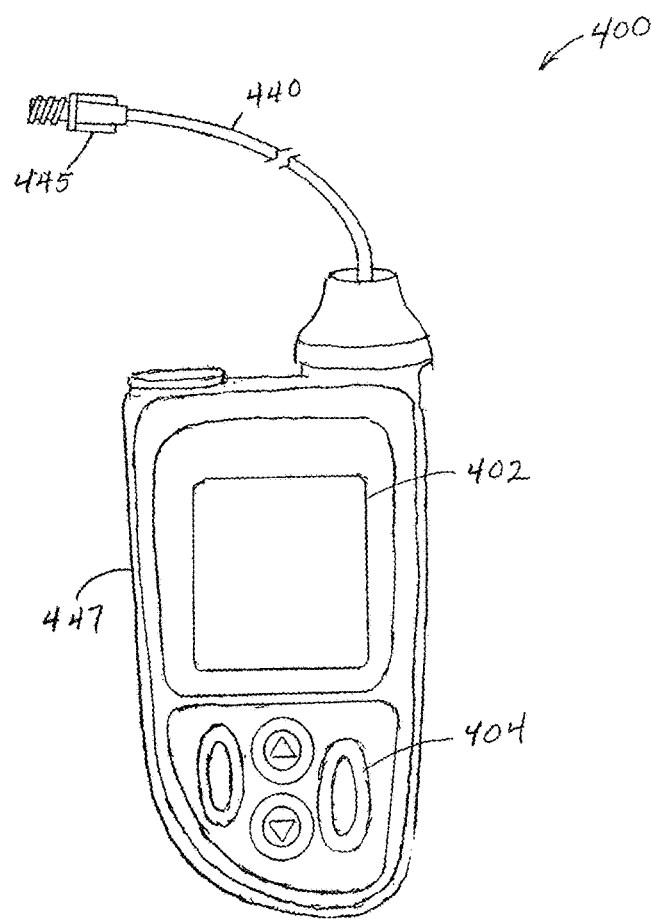
FIG. 4 is an illustration of a BG management device that includes an insulin pump.

FIG. 4 is an illustration of a BG management device 400 that includes an insulin pump. The BG management device 400 includes a cassette or cartridge of insulin and tubing 440 connectable to a patient such as by a Luer lock 445. The BG management device 400 includes a user interface that may include a display 402 operatively coupled to a controller 115. The user interface may also include one or more keys 404.

Returning to FIG. 3, the blood glucose data obtained during the basal insulin rate test may be produced by a second device separate from the BG management device 300. The controller 115 displays user instructions for the basal rate test. The user interface 105 and the input 110 are configured to receive the sampled blood glucose data entered manually by the user through the user interface 105. The controller 115 may periodically prompt the user to enter a blood glucose value at different times during the test, or to enter the blood glucose data all at once after the test.

Figure 5:
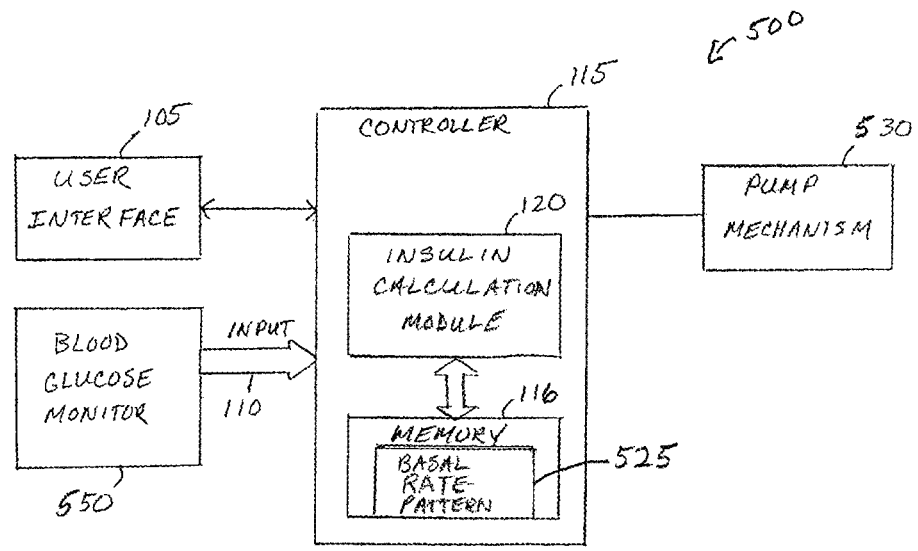
FIG. 5 is another block diagram of portions of a BG management device that includes a pump mechanism.

FIG. 5 is another block diagram of portions of a BG management device 500 that includes a pump mechanism 530 and delivers basal insulin according to one or more basal rate patterns 525 stored in memory 116. A blood glucose monitor, or GM 550, is communicatively coupled to the input 110. The input 110 is configured to receive the sampled blood glucose data from the GM 550. In some examples, the GM 550 is included in the BG management device 500 and is coupled to the input 110. In some examples, the GM 550 is included in a second device. The input 110 may receive the blood glucose data during the basal rate test or after the test is run. The input 110 may include a communication port, such as communication port 447 located on the rear face of the device in FIG. 4, and the GM 550 is communicatively coupled to the input 110 by the communication port 447. In some embodiments, the communication port 447 is a wired port such as a serial interface or bus interface for communicating with the second device. In some embodiments, the communication port 447 is a wireless port such as an infrared (IR) communication port or a radio frequency (RF) communication port. The input 110 wirelessly receives the sampled blood glucose data from the second device.

Returning to FIG. 5, in some embodiments, the GM 550 is a continuous GM and automatically collects the sampled blood glucose data. For example, the GM 550 may include a blood glucose sensor. The blood glucose sensor produces a blood glucose signal representative of a blood glucose level of the patient. The GM 550 samples the blood glucose signal to obtain the sampled blood glucose data.

In some embodiments, the GM 550 may need to prompt the user to begin a blood glucose measurement. For example, the GM 550 may require diabetes test strips to take a blood glucose measurement. The controller 115 prompts the user, via a display, to begin a blood glucose measurement using the GM 550. The user then provides a new test strip to the GM 550 when prompted during the basal rate test. In another example, the GM 550 may include a drum of diabetes test strips and the user advances the drum to a fresh or unused test strip when prompted by the controller 115. The controller 115 may display a recommended basal rate after the basal rate test. The controller 115 may also communicate a recommended change in the basal rate to the second device via a communication port.

Figure 6:
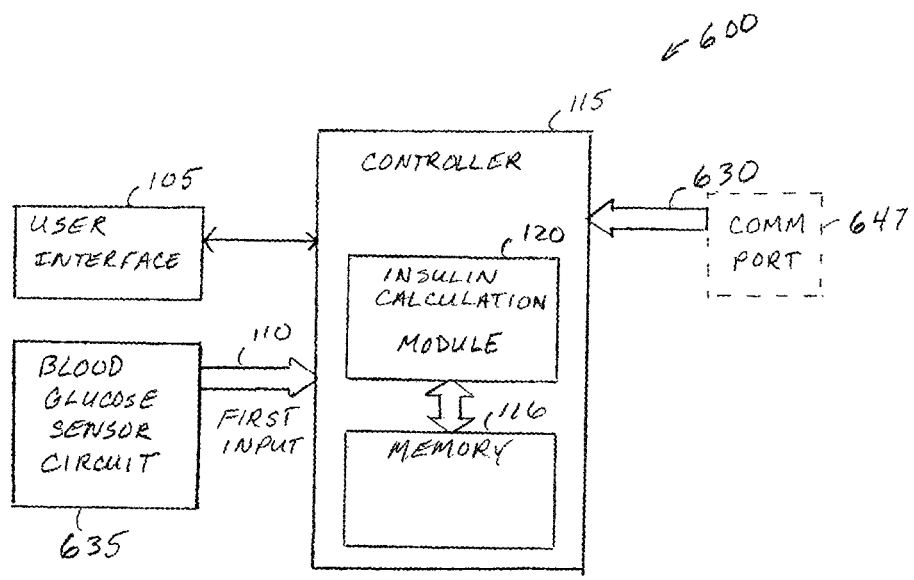
FIG. 6 is a block diagram of a BG management device that includes a blood glucose sensor circuit.

According to some embodiments, the BG management device is a GM. FIG. 6 is a block diagram of a BG management device 600 that includes a blood glucose sensor circuit 635 operatively coupled to the input 110. The blood glucose sensor circuit 635 produces a blood glucose signal representative of a blood glucose level of the patient and provides the sampled blood glucose data to input 110. In some embodiments, the blood glucose sensor circuit 635 includes an implantable blood glucose sensor. In some embodiments, the blood glucose sensor includes a percutaneous blood glucose sensor. The blood glucose sensor circuit 635 may include signal conditioning circuits, such as for signal filtering and signal amplification for example. If an implantable blood glucose sensor is used, the blood glucose sensor circuit 635 may include a communication circuit configured to receive blood glucose data wirelessly, such as by RF communication.

The BG management device 600 includes a second input 630 communicatively coupled to the controller 115. The second input 630 receives information related to basal insulin delivery, such as one or more basal rate patterns used during the basal rate test. The information related to insulin delivery may be received into a memory 116. The insulin calculation module 120 determines at least one of an amount of insulin over-delivered and an amount of insulin under-delivered during the basal rate test using the insulin delivery information and the sampled blood glucose data. The BG management device 600 may include a communication port 647 coupled to the second input 630. The communication port 647 receives the information related to insulin delivery from a second device. In some embodiments, the communication port 647 is a wired port such a serial interface or bus interface. In some embodiments, the communication port 647 is a wireless port such as an infrared (IR) communication port or a radio frequency (RF) communication port. The second input 630 wirelessly receives the insulin delivery data from the second device. As an example, the second device may be an insulin pump. The insulin calculation module 120 may determine changes to the basal rate pattern used to deliver basal insulin during the basal rate test. The controller 115 communicates recommended changes through the communication port 647 or may display the recommended changes on a display.

In some embodiments, the user interface 105 and the second input 630 are configured to receive the information related to insulin delivery by a user manually entering the information through the user interface 105. The insulin delivery information may be obtained from a pump for example. The controller 115 may display any recommended changes to the basal rate pattern.

Figure 7:
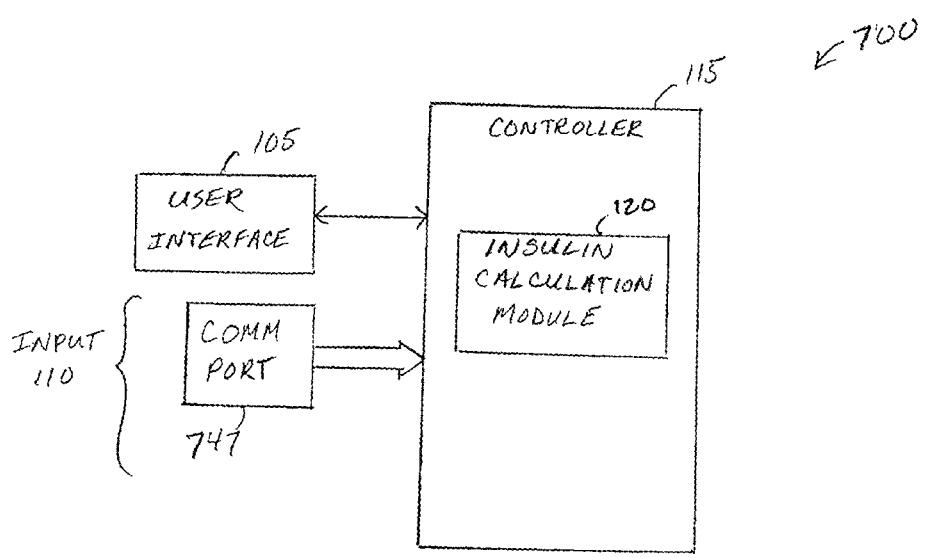
FIG. 7 is a block diagram of portions of another example of a BG management device.

FIG. 7 is a block diagram of portions of another example of a BG management device 700. BG management device 700 includes neither a GM nor an insulin pump. The BG management device 700 includes a user interface 105, an input 110, and a controller 115 communicatively coupled to the input 110 and the user interface 105. The input 110 includes at least one communication port 747 configured for receiving sampled blood glucose information. The communication port 747 may provide a wired connection to a second device, or the communication port 747 may provide a wireless connection to a second device. The sampled blood glucose information may include at least one time-stamp in order to align the sampled blood glucose information to information related to insulin delivery.

The insulin delivery information may be received through the same communication port 747 or a second communication port. The communication ports may be any combination of wired or wireless communication ports. The insulin delivery information includes information related to basal insulin delivered according to a basal rate pattern, and may include at least one time-stamp to align the insulin delivery information with the blood glucose information. The insulin calculation module 120 determines at least one of an amount of insulin over-delivered and an amount of insulin under-delivered during the basal rate test using the insulin delivery information and the sampled blood glucose data. The insulin calculation module 120 may recommend changes to the basal rate pattern. The controller 115 may communicate recommended changes to the basal rate pattern through the communication port 747 and/or the controller 115 may display the recommended changes.

Method Embodiments

Figure 8:
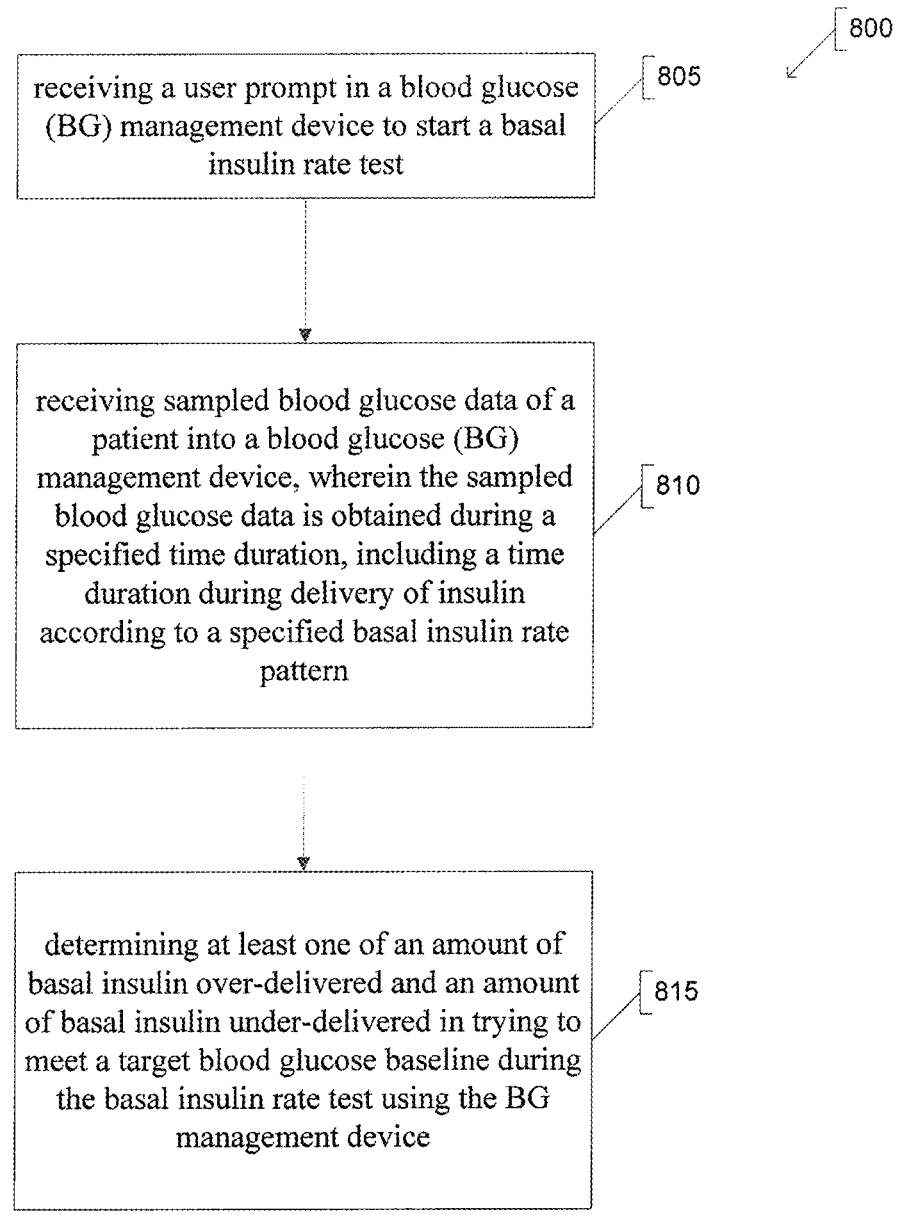
FIG. 8 is a flow diagram of a method of using a BG management device to execute a basal rate test.

FIG. 8 is a flow diagram of a method 800 of using a BG management device to execute a basal rate test. At block 805, a user prompt is received in a BG management device to start a basal insulin rate test. The user interface may include a push-button, keypad, or mouse. The user interface may also include a display to display one or more instructions for the user to execute the basal rate test, and to display to display any recommend changes to a basal rate or a basal rate pattern. In some embodiments, the method 800 includes displaying instructions for the basal insulin rate test using the BG management device.

At block 810, sampled blood glucose data is received in the BG management device. The blood glucose data is obtained from a patient during a specified time duration, including a time during delivery of insulin according to a basal insulin rate pattern that is part of the basal rate test.

At block 815, at least one of an amount of basal insulin over-delivered or an amount of basal insulin under-delivered is determined. The over-delivery and/or under-delivery occur in trying to meet a target blood glucose baseline during the basal insulin rate test. In some embodiments, the method 800 includes the BG management device automatically recommending changes, if any, to the basal insulin rate pattern.

In some embodiments, the method 800 includes determining an amount of basal insulin over-delivered or an amount of basal insulin under-delivered using the correction factor and the variance from the blood glucose baseline concentration. In some embodiments, the amount of insulin over or under-delivered is determined using an adjusted correction factor. The correction factor may be adjusted using a correction factor multiplier. In some embodiments, recommending a change may include spreading out the change to the basal delivery rate pattern out over a time duration corresponding to a time to a change in direction of the blood glucose data values.

In some embodiments, the method includes recommending changes to the basal insulin rate pattern that precede any actual times of over-delivery or under-delivery by a time duration that compensates for a delay or lag time associated with subcutaneous insulin delivery. In some embodiments, the method 800 includes calculating the lag time using at least one of i) the type of insulin delivered during the basal rate test, ii) the activity level of the patient at the time the basal rate test takes place, iii) the fitness level of the patient, and iv) the method of obtaining the blood glucose data, e.g., whether the blood glucose data was obtained from blood or from interstitial fluid. In some embodiments, the method 800 includes calculating the lag time using blood glucose data obtained prior to the basal insulin rate test.

According to some embodiments, the BG management device includes an insulin pump. The method 800 includes determining an amount of active insulin (IOB) at the beginning of the basal rate test. The IOB may be determined before delivering basal insulin according to a basal rate pattern of the basal insulin test. In some embodiments, if an amount of active insulin is above a specified threshold active insulin amount, the BG management device may cancel the basal rate test. In some embodiments, the method 800 includes canceling the basal insulin rate test if an insulin bolus dose, such as a correction bolus or a carbohydrate bolus, is delivered during the basal insulin rate test.

According to some embodiments, the BG management device includes an insulin pump and a GM. The method 800 includes automatically receiving the sampled blood glucose data from the blood glucose monitor. In some embodiments, the BG management device includes the insulin pump and the blood glucose data is obtained using a separate device. The method 800 includes receiving the sampled blood glucose data into the BG management device from the separate device through a communication port. The communication port may be a wireless port or a wired port. The separate device may be a continuous GM.

In some embodiments, the separate device may be a GM that requires some action by the user to obtain a blood glucose reading. For example, the GM may require the user to place a test strip into the GM in order to obtain a glucose reading. In some embodiments, the method 800 may include prompting the user through a user interface to obtain blood glucose data using the separate device. The prompting may be periodic during the basal rate test.

In some embodiments, the blood glucose data obtained from the separate device is entered manually into the BG management device. The method 800 includes the BG management device receiving the blood glucose data through the user interface. The user interface is configured for manual entry of blood glucose data, such as by including a keypad and a display. The user reads the blood glucose data from the separate GM and manually enters the blood glucose data into the BG management device. In some embodiments, the method 800 includes the BG management device periodically prompting the user to manually enter a blood glucose value during the basal rate test.

According to some embodiments, the BG management device includes a GM and does not include an insulin pump. The basal insulin is delivered according to a basal rate pattern using a second separate device. The sampled blood glucose data is received automatically using the included GM. The method 800 further includes receiving information related to insulin delivery into the BG management device from the separate device, including an amount of insulin delivered according to the basal rate pattern. The BG management device determines at least one of an amount of insulin over-delivered and an amount of insulin under-delivered during the basal rate test using the insulin delivery information and the sampled blood glucose data.

In some embodiments, the method 800 includes receiving the insulin delivery information into the BG management device through a communication port. As part of the basal rate test, the BG management device may communicate a recommended change to the basal rate pattern to the separate device using the communication port. This is useful if the separate device is an insulin pump. In some embodiments, the method 800 includes receiving the insulin delivery information into the BG management device by manually entering the insulin delivery information. The information is manually entered via a user interface on the BG management device. Any recommended changes to the basal rate pattern may be displayed on the BG management device.

According to some embodiments, the BG management device does not include a GM or an insulin pump. The basal insulin is delivered according to a basal rate pattern using a second separate device, such as an insulin pump for example. The method 800 includes providing insulin delivery information, such as an amount of insulin delivered according to the basal rate pattern, to the BG management device using the second device.

The BG management device receives sampled blood glucose data from the second separate device or a third device. At least one of the insulin delivery information and the sampled blood glucose data includes a time-stamp to allow for alignment of the insulin delivery information and the blood glucose data. For example, the time-stamp for the insulin delivery may be the time at which the basal rate changes. The BG management device determines at least one of an amount of insulin over-delivered and an amount of insulin under-delivered during the basal rate test using the insulin delivery information and the sampled blood glucose data. Any recommended changes to the basal rate pattern may be displayed on the BG management device.

In some embodiments, the method 800 includes executing the basal insulin rate test during a substantially same time on multiple days. In some examples, the method 800 includes executing an overnight basal rate test. In some examples, the method includes executing an overnight basal rate test that includes an overnight basal rate calibration and verification technique.

Figure 9:
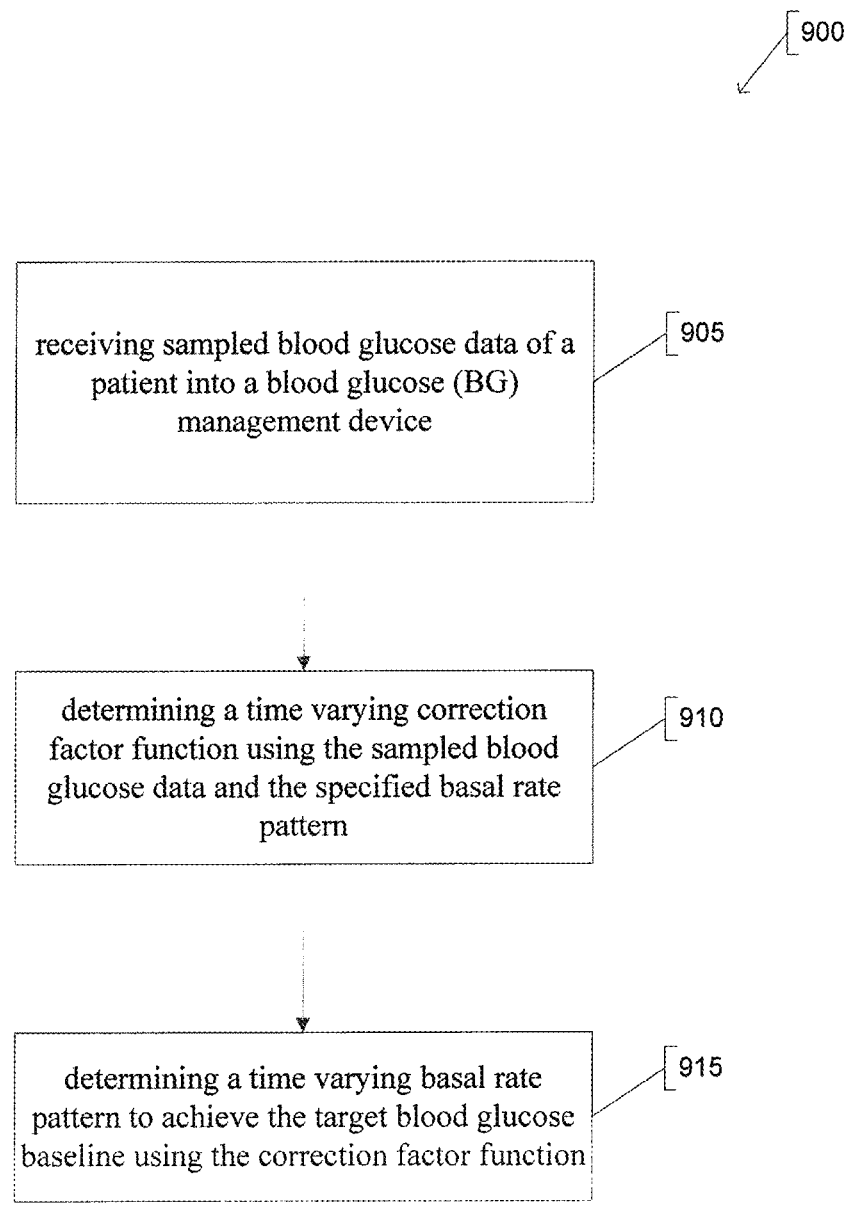
FIG. 9 is a flow diagram of another method of using a BG management device to execute a basal rate test.

FIG. 9 is a flow diagram of another method 900 of using a BG management device to execute a basal rate test. At block 905, sampled blood glucose data is received in a BG management device. The blood glucose data may be obtained from a patient during a specified time duration according to a specified basal insulin rate pattern that is part of the basal rate test. At block 910, a time varying correction factor c(t) is determined using the sampled blood glucose data and the specified basal insulin rate pattern. At block 915, a time varying basal rate pattern b(t) is determined. The time varying basal rate pattern is to achieve the target blood glucose baseline. The target blood glucose baseline may be a constant or a time varying function g(t). In some embodiments, the method 900 includes generating a change to the test-specified basal rate pattern using the determined time varying basal rate pattern b(t). In some embodiments, the method includes recommending a change to the test-specified basal rate pattern, such as by using a display for example.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:

1. An infusion pump system, comprising:
   a pump mechanism configured to facilitate delivery of a medicament to a patient;
   a memory configured to store at least one basal rate pattern and a target glucose level for the patient, the at least one basal rate pattern configured to vary a basal rate of medicament delivery to the patient by a time of day;
   an input configured to receive glucose level data of the patient from a continuous glucose monitor; and
   a processor functionally linked to the pump mechanism, the memory and the input, the processor configured to execute a basal rate test, the basal rate test including:
      determining an amount of insulin on board in the patient;
      causing the pump mechanism to deliver the medicament to the patient according to the at least one basal rate pattern;
      receiving glucose level data of the patient from the continuous glucose monitor;
      comparing the glucose level data of the patient to the target glucose baseline;
      determining whether any instances of the glucose level of the patient rising above the target glucose baseline occur and whether any instances of the glucose level of the patient falling below the target glucose baseline occur during the basal rate test;
      determining an amount of medicament over-delivered for each of the instances where the glucose level of the patient falls below the target glucose baseline;
      determining an amount of medicament under-delivered for each of the instances where the glucose level of the patient rises above the target glucose baseline; and
      modifying the at least one basal rate pattern based on the amounts of medicament over-delivered and under-delivered during the basal rate test, and
   wherein the processor is configured to terminate the basal rate test if, during the basal rate test, the glucose level of the patient is outside of a predefined range of glucose levels, an amount of insulin on board in the patient determined by the processor is above a threshold level, or if a bolus delivery of medicament is initiated by the processor.

2. The infusion pump system of claim 1, further comprising a user interface, and wherein the processor is further configured to:
   present instructions on the user interface relating to patient actions during the basal rate test.

3. The infusion pump system of claim 1, wherein the processor is further configured to store the modified basal rate pattern in the memory.

4. The infusion pump system of claim 1, wherein the modified basal rate pattern adjusts the delivery of medicament from the at least one basal rate pattern by a time duration that compensates for a lag time associated with subcutaneous insulin delivery.

5. The infusion pump system of claim 1, where the target glucose baseline is a single glucose level value.

6. The infusion pump system of claim 5, wherein the at least one basal rate pattern is modified only when there were instances when the glucose level of the patient was above or below the target glucose level by a specified range during the basal rate test.

7. The infusion pump system of claim 5, wherein the target glucose baseline is a constant value.

8. The infusion pump system of claim 5, wherein the target glucose baseline varies as a function of time.

9. The infusion pump of claim 1, wherein the processor is configured to determine the amounts of medicament overdelivered and the amounts of medicament under-delivered by calculating the amounts using a patient-specific correction factor and a variance of the glucose level of the patient from the target glucose baseline for each instance.

10. The infusion pump system of claim 9, wherein the processor is further configured to apply a correction factor multiplier to the patient-specific correction factor to reduce the calculated amounts of medicament.

11. A method of performing a basal rate test, comprising:
storing in a memory of an infusion pump at least one basal rate pattern and a target glucose baseline for a patient, the at least one basal rate pattern configured to vary a basal rate of medicament delivered to the patient with a pump mechanism of the infusion pump by a time of day;
determining an amount of insulin on board in the patient;
causing the pump mechanism to deliver the medicament to the patient according to the at least one basal rate pattern;
receiving glucose level data of the patient from a continuous glucose monitor;
comparing the glucose level data of the patient to the target glucose baseline;
determining whether any instances of the glucose level of the patient rising above the target glucose baseline occur and whether any instances of the glucose level of the patient falling below the target glucose baseline occur during the basal rate test;
determining an amount of medicament over-delivered for each of the instances where the glucose level of the patient falls below the target glucose baseline;
determining an amount of medicament under-delivered for each of the instances where the glucose level of the patient rises above the target glucose baseline; and
modifying the at least one basal rate pattern to an adjusted basal rate pattern based on the amounts of medicament over-delivered and under-delivered during the basal rate test, and
further comprising terminating the basal rate test if, during the basal rate test, the glucose level of the patient is outside of a predefined range of glucose levels, a determined amount of insulin on board in the patient is above a threshold level, or if a bolus delivery of insulin is initiated.

12. The method of claim 11, further comprising presenting instructions relating to patient actions during the basal rate test on a user interface of the infusion pump.

13. The method of claim 11, further comprising storing the modified basal rate pattern in the memory.

14. The method of claim 11, wherein modifying the at least one basal rate pattern includes modifying the delivery of medicament by a time duration that compensates for a lag time associated with subcutaneous insulin delivery.

15. The method of claim 11, where the target glucose baseline is a single glucose level value.

16. The method of claim 15, wherein the at least one basal rate pattern is modified only when there were instances when the glucose level of the patient was above or below the target glucose level by a specified range during the basal rate test.

17. The method of claim 15, wherein the target glucose baseline is a constant value.

18. The method of claim 15, wherein the target glucose baseline varies as a function of time.

19. The method of claim 11, wherein determining the amounts of medicament over-delivered and the amounts of medicament under-delivered includes calculating the amounts using a patient-specific correction factor and a variance of the glucose level of the patient from the target glucose baseline for each instance.

20. The method of claim 19, further comprising applying a correction factor multiplier to the patient-specific correction factor to reduce the calculated amounts of medicament.

* * * * *